(12) United States Patent
Vitiello et al.

(10) Patent No.: US 8,323,190 B2
(45) Date of Patent: Dec. 4, 2012

(54) COMPREHENSIVE NEUROMUSCULAR PROFILER

(75) Inventors: Marco N. Vitiello, Miami, FL (US); Charles Dean Cyphery, Albuquerque, NM (US); Lance H. Butler, Albuquerque, NM (US)

(73) Assignee: Med-Tek LLC, Coconut Grove, FL (US)

( * ) Notice: Subject to any disclaimer, the term of this patent is extended or adjusted under 35 U.S.C. 154(b) by 1514 days.

(21) Appl. No.: 10/504,031

(22) PCT Filed: Jul. 9, 2004

(86) PCT No.: PCT/US2004/022210
§ 371 (c)(1),
(2), (4) Date: Apr. 19, 2005

(87) PCT Pub. No.: WO2005/006956
PCT Pub. Date: Jan. 27, 2005

(65) Prior Publication Data
US 2006/0058699 A1 Mar. 16, 2006

Related U.S. Application Data

(60) Provisional application No. 60/485,979, filed on Jul. 9, 2003.

(51) Int. Cl.
*A61B 5/00* (2006.01)
(52) U.S. Cl. ............... 600/301; 600/300; 73/379.01
(58) Field of Classification Search .......... 600/300–301, 600/547, 587–595; 324/207.11–207.26; 73/379.01–379.02
See application file for complete search history.

(56) References Cited

U.S. PATENT DOCUMENTS

| | | | | |
|---|---|---|---|---|
| 3,569,705 A * | 3/1971 | Kaminsky | ............ | 250/251 |
| 4,375,674 A * | 3/1983 | Thornton | ............ | 702/41 |
| 4,664,130 A * | 5/1987 | Gracovetsky | ............ | 600/594 |
| 4,849,692 A * | 7/1989 | Blood | ............ | 324/207.26 |
| 4,945,305 A * | 7/1990 | Blood | ............ | 324/207.17 |
| 5,091,948 A * | 2/1992 | Kametani | ............ | 704/248 |
| 5,112,296 A * | 5/1992 | Beard et al. | ............ | 602/28 |
| 5,353,354 A * | 10/1994 | Keller et al. | ............ | 382/128 |
| 5,453,686 A * | 9/1995 | Anderson | ............ | 324/207.17 |
| 5,462,065 A * | 10/1995 | Cusimano | ............ | 600/595 |
| 5,513,651 A * | 5/1996 | Cusimano et al. | ............ | 600/595 |
| 5,524,637 A * | 6/1996 | Erickson | ............ | 600/592 |
| 5,551,445 A * | 9/1996 | Nashner | ............ | 600/595 |
| 5,846,086 A * | 12/1998 | Bizzi et al. | ............ | 434/247 |
| 5,885,976 A * | 3/1999 | Sandyk | ............ | 514/159 |
| 5,929,782 A * | 7/1999 | Stark et al. | ............ | 340/870.01 |
| 6,004,312 A * | 12/1999 | Finneran et al. | ............ | 600/546 |
| 6,083,156 A * | 7/2000 | Lisiecki | ............ | 600/301 |
| 6,148,280 A * | 11/2000 | Kramer | ............ | 702/153 |
| 6,427,079 B1 * | 7/2002 | Schneider et al. | ............ | 600/424 |
| 6,450,953 B1 * | 9/2002 | Place et al. | ............ | 600/300 |
| 6,491,647 B1 * | 12/2002 | Bridger et al. | ............ | 600/585 |

(Continued)

*Primary Examiner* — Sam Yao
*Assistant Examiner* — Bobby Soriano
(74) *Attorney, Agent, or Firm* — McDermott Will & Emery LLP

(57) ABSTRACT

A Comprehensive Neuromuscular Profiler (CNMP) allows the observation of human and equine muscle functionality and characteristics. The CNMP consists of an integrated system which combines EMG technology, electromagnetic range-of-motion (ROM) technology, and functional capacity sensors. Output signals from the devices are digitized and stored in computer memory. The data may be transmitted to a server computer for further analysis. The server computer examines the data to determine patterns and consults an expert database to determine a diagnosis based on the patterns and combinations of patterns detected.

26 Claims, 16 Drawing Sheets

U.S. PATENT DOCUMENTS

| | | | |
|---|---|---|---|
| 6,897,788 B2 * | 5/2005 | Khair et al. | 340/870.16 |
| 7,214,197 B2 * | 5/2007 | Prass | 600/554 |
| 7,242,988 B1 * | 7/2007 | Hoffberg et al. | 700/28 |
| 7,353,064 B2 * | 4/2008 | Gliner et al. | 607/45 |
| 7,375,521 B1 * | 5/2008 | Damadian et al. | 324/307 |
| 2001/0041846 A1 * | 11/2001 | Appel et al. | 600/546 |
| 2002/0143277 A1 * | 10/2002 | Wood et al. | 600/595 |
| 2002/0170193 A1 * | 11/2002 | Townsend et al. | 33/512 |
| 2002/0198473 A1 * | 12/2002 | Kumar et al. | 600/595 |
| 2003/0088185 A1 * | 5/2003 | Prass | 600/546 |
| 2003/0135129 A1 * | 7/2003 | Cusimano et al. | 600/546 |
| 2003/0139692 A1 * | 7/2003 | Barrey et al. | 600/595 |
| 2004/0138583 A1 * | 7/2004 | Galea | 600/547 |
| 2004/0193068 A1 * | 9/2004 | Burton et al. | 600/544 |
| 2004/0214348 A1 * | 10/2004 | Nicholson et al. | 436/518 |
| 2004/0220490 A1 * | 11/2004 | Appel et al. | 600/546 |
| 2005/0197776 A1 * | 9/2005 | Makela et al. | 702/4 |
| 2006/0018360 A1 * | 1/2006 | Tai et al. | 374/121 |

\* cited by examiner

COMPREHENSIVE NEUROMUSCULAR PROFILER

CROSS-REFERENCE TO RELATED APPLICATIONS

This application claims the benefit of U.S. Provisional Patent Application No. 60/485,979 filed on Jul. 9, 2003 entitled Comprehensive Neuromuscular Profiler.

FIELD OF THE INVENTION

The Invention relates to the collection of data for an expert diagnostic system, and more specifically, to the collection of data for a comprehensive neuromuscular profiler for monitoring general muscular status and assessing muscle and soft tissue injuries. The Invention is an integrated biomechanical information gathering and expert analysis system for evaluating health and functioning of human muscles and the joints operated by the muscles.

DESCRIPTION OF THE RELATED ART

The range and dynamics of motion of a patient, the strength of the patient's muscles and the electrical characteristics of the muscles provide information useful to a clinician making treatment decisions for a patient. The same information also may be useful to determine the existence, severity or cause of an injury and whether an injury is acute or chronic for purposes of determining questions of insurance or other liability.

Soft tissue injuries and pathology may occur in any area of the body and may include repetitive stress injuries, injuries to muscles, myofascial injuries, damage to vertebral disks, radiculopathy, and others. These injuries may be difficult to diagnose and hence may be difficult to treat properly.

Electromyography ("EMG") has proved to be useful in diagnosing some injuries, especially those that are related to repetitive motion. More generally, EMG is useful in diagnosing injuries which can be identified from the examination of static muscle activity. However, EMG cannot provide a comprehensive examination of muscular compensation patterns. These patterns are a key aspect of identifying and properly diagnosing myofascial injuries.

Range-of-motion ("ROM") testing has also been used to identify injury by examining the characteristics of dynamic muscle activity. However, like EMG testing, ROM testing has limitations in providing a full examination of compensation patterns, and is not adequately effective as a stand-alone method for injury diagnosis.

There have been attempts to integrate EMG and ROM technology to provide a more comprehensive diagnosis process.

SUMMARY OF THE INVENTION

The Invention integrates several muscle and joint monitoring measurements into a single apparatus so that an expert diagnosis may be provided based on the data collected by the apparatus. The apparatus gathers four types of information, which may be collected simultaneously or serially: motion, video, muscle capacity and electromyography ("EMG").

Motion information is collected by remote sensing technology. A suitable technology is pulsed DC magnetic field sensing, although other sensing technologies such as optical sensing or AC magnetic field sensing may be used. In pulsed DC magnetic field sensing, an electromagnetic transmitter generates a pulsed electromagnetic field. One or more ROM sensors, each comprising three axis ring-core flux-gate magnetometer, are attached to the patient. Changes in the electromagnetic field are detected by the ROM sensors. The detected changes in the electromagnetic field are measured and analyzed by a ROM signal processor, which translates the ROM signal from the ROM sensors into information defining the position and motion of the ROM sensors and hence of the patient. The motions measured include the range of motion ("ROM") and also may include the dynamic motion of the patient within the ROM.

Muscle strength measurements are collected by having the patient exert force using the muscle in question against a fixed object and measuring the force exerted by the muscle. Grip strength, finger pinch strength and isometric functional test measurements are made by having the patient grip, pinch or otherwise exert force on the appropriate sensors. EMG measurements are collected by attaching electrodes (referred to in this application as "EMG sensors") to the patient and recording electrical activity of the muscles in question.

The signals collected from the various sensors are digitized and recorded in the memory of a client computer. The client computer may communicate the data to a server computer over a computer network. Software resident in the server computer includes an expert system that evaluates the data for patterns and for combinations of patterns among the types of data collected. The server computer is programmed to compare the patterns, or lack of patterns, detected in the data to predetermined patterns associated with injuries, pathologies, and lack of injuries and pathologies. The expert system may diagnose, for example, sprains, strains, vertebral disk injury and radiculopathies. The expert system also may determine whether the injury is of recent origin, thereby distinguishing acute from chronic injury. The expert system may look for changes in other muscles or behaviors compensating for pain or loss of use as the result of pathology or injury. An issue with the interpretation of EMG results historically has been the variability in interpretation among different healthcare professionals. The expert system serves to resolve that variability and to achieve consistency of interpretation. The server computer assigns a patient profile to the patient based on the diagnosis made by the server computer. The server computer may communicate the patient profile to the client computer for display to the user. Alternatively, the patient profile may be communicated to any other authorized person. The functions of the client and server computers may be integrated into a single stand-alone computer.

The client computer is programmed to administer any of several "protocols" to the patient and to record the resulting data. A "protocol" is a sequence of tasks, or tests, that the patient performs while the appropriate sensors collect data concerning the portion of the patient's body in question. Each protocol specifies the identity, number and location of the sensors to be used. The client computer is programmed to provide step-by-step instructions to the patient and to the technician, or user, administering the protocol to the patient. The client computer is programmed to collect and record the appropriate sensor data for each protocol. For purposes of this application, the specific data specified to be collected for a particular protocol is referred to as "protocol data."

As used in this application, the term "client computer" means any computer or system of computers capable of communicating with another computer over a computer network. The term "server computer" means any computer or system of computers that is capable of receiving a communication over a computer network from a client computer and performing an evaluation based on the received communication.

The apparatus may be equipped with automated, interactive instructions to an operator who has no or little knowledge of anatomy. The apparatus therefore may be operated at a relatively modest cost. The apparatus may be equipped with a video camera or other remote imaging technology to allow a physician or other medical personnel to remotely monitor the procedure and to create a visual record of the tests performed and the patient's response to the tests. The apparatus may be equipped with the capacity to automatically generate billing forms or electronic files, such as the HCFA form or file.

The server computer may be programmed to generate appropriate billing files or forms and to transmit those billing files or forms to a payor. The server computer also may be programmed to compare the patient profile assigned to a patient to predetermined criteria for disability ratings.

BRIEF DESCRIPTION OF THE DRAWINGS

The accompanying drawings, which are incorporated in and form a part of the specification, illustrate the embodiments of the present invention and, together with the description, serve to explain the principles of the invention.

DESCRIPTION OF THE PREFERRED EMBODIMENT

Figure 1:
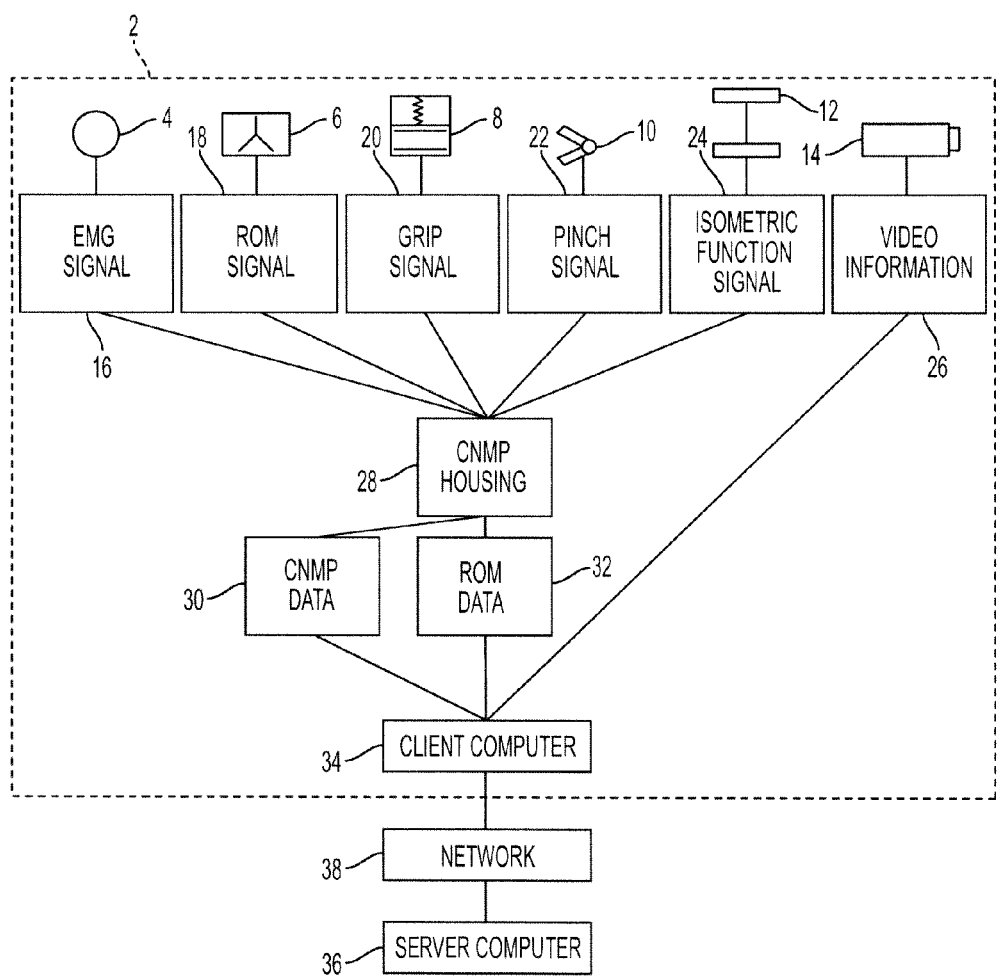
FIG. 1 is block diagram of the Invention and the information collected by the Invention.

As shown by FIG. 1, the 'Comprehensive Neuromuscular Profiler' ("CNMP") 2 of the present invention is an integrated data acquisition device for detecting, recording and analyzing information relating to a patient. The CNMP 2 comprises surface electromyography ("EMG") sensors 4, range of motion ("ROM") sensor 6, grip strength sensor 8, finger pinch strength sensor 10, isometric function capacity sensor 12, and a video camera 14, all connected to the client computer 34. The sensors respectively generate EMG signals 16, ROM signal 18, grip signal 20, pinch signal 22, isometric function signal 24 and video information 26. Signals generated by the sensors are conveyed to a CNMP housing 28. In the CNMP housing 28, the EMG signals 16, isometric function signal 24, grip signal 20 and pinch signal 22 are processed and digitized to become EMG data, isometric function data, grip data and pinch data, referred to collectively in this application as "CNMP data" 30. The ROM signal 18 also is processed in the CNMP housing 28 to become ROM data 32. The video information 26 from the video camera 14 is passed directly to a first client computer 34; which may be a personal computer. CNMP data 30 and ROM data 32 are transmitted from the CNMP housing 28 to the first client computer 34, The CNMP data 30, ROM data 32 and video information 26 may be transmitted to a server computer 36 over a network 38.

Figure 2:
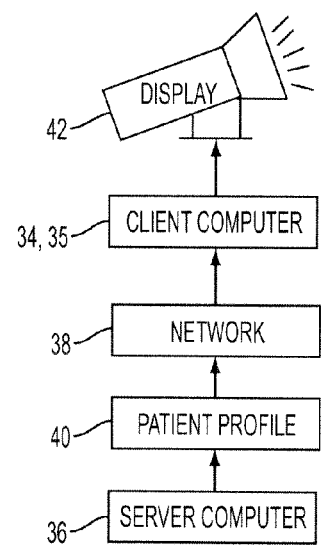
FIG. 2 is a schematic diagram of the connection of the client computer to the server computer.

As illustrated by FIG. 2, the server computer 36 evaluates the CNMP data 30 and ROM data 32. The server computer 36 assigns a patient profile 40 to the patient based on the evaluation and transmits the patient profile 40 to a second client computer 35 for display 42 to an authorized user such as an insurer or employer. Alternatively, some or all of the data analysis may be performed by the first client computer 34 and some or all of the generation of patient profile 40 may occur within the first client computer 34.

Figure 3:
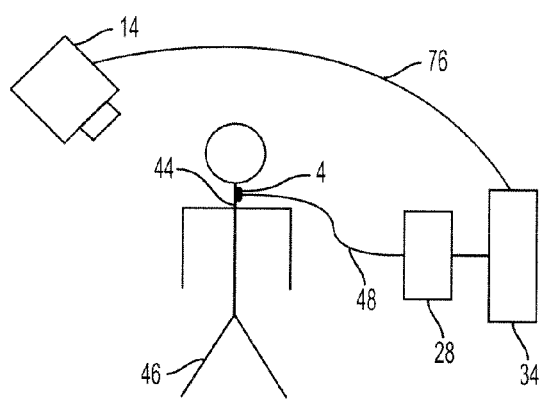
FIG. 3 is a schematic diagram of the collection of EMG data.

Generation of EMG signal 16 by the EMG sensors 4 is illustrated by FIG. 3. As shown by FIG. 3, a grounding sensor and one or more differential pairs of EMG sensors 4 are attached to predetermined locations 44, as specified in Table 1 below, on patient 46. A total of thirty-six EMG sensors 4 (18 signal pairs) may be attached to the patient 46 using techniques well known in the art. An EMG sensor 4 is connected by EMG cable assembly 48 to CNMP housing 28. Two EMG cable assemblies 48 are provided. Each EMG cable assembly 48 is conventional and comprises nineteen individual coaxial sensor cables (9 pairs of differential leads) plus a single ground sensor. Each EMG cable assembly 48 is able to accommodate nine EMG signal pairs and the ground sensor 4 and is capable of conveying these nine separate EMG signal pairs 16. Each coaxial cable is shielded to help eliminate any cross channel noise. The CNMP housing 28 is capable of processing each of the eighteen channels of EMG signals 16 generated by the EMG sensors 4 and samples the EMG signals 6 at a rate of 15 KHz. The Invention is not limited to thirty-six EMG sensors 4 (18 pairs), and any number of EMG sensors 4 may be utilized.

The appropriate number of EMG sensors 4 is specified for each test to be performed on patient 46. The EMG sensors 4 are conventional silver chloride electrodes. Pairs of EMG sensors 4 are selected for each predetermined location 44 on the patient 46. The predetermined locations 44 on the patient 46 are selected to provide EMG signals 4 relating to the muscles in question and relating to muscles that, may be compensating for the muscles in question.

Figure 4:
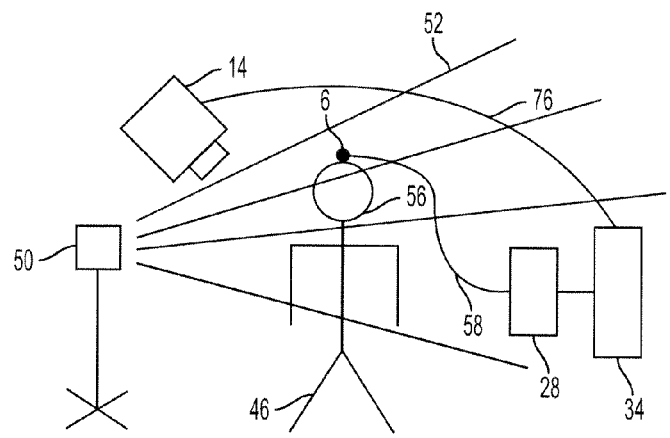
FIG. 4 is a schematic diagram of the collection of ROM data.
Figure 8:
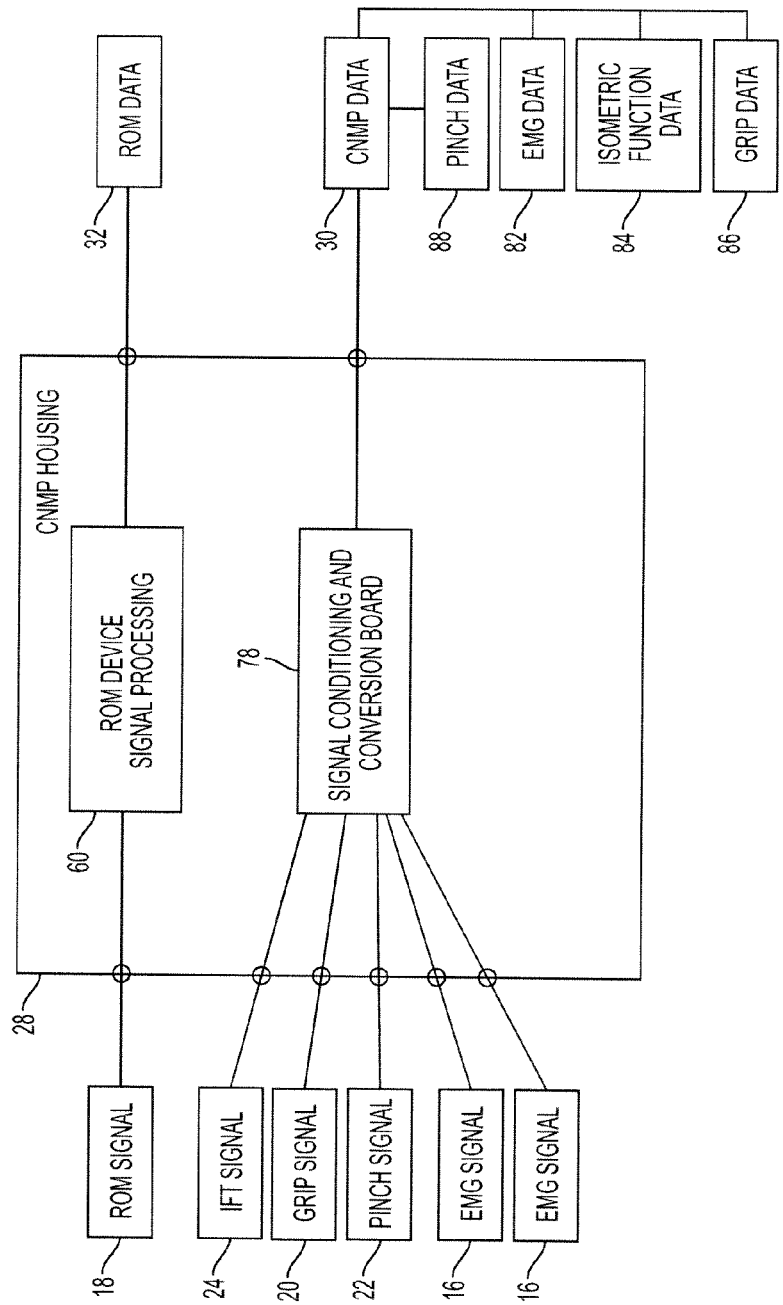
FIG. 8 is a block diagram of signal flow through the CNMP housing.

FIG. 4 illustrates generation of a range-of-motion ("ROM") signal 18. A ROM transmitter 50 creates an electromagnetic field 52 in the vicinity of patient 46. A ROM sensor 6 is attached to the body of patient 46 at a ROM sensor predetermined location 56, as specified in Table 2, below. The ROM sensor 6 generates a ROM signal 18 in response to a position of the ROM sensor 6 within the electromagnetic field 52. The ROM sensor 6 is connected by a ROM sensor cable 58 to the CNMP housing 28. A ROM signal processor 60, as shown by FIG. 8, processes the ROM signal 18 into ROM data 32.

The electromagnetic field 52 generated by the ROM transmitter 50 is a DC-based pulsed electromagnetic field. A single ROM sensor 6 is adequate for purposes of the Invention, although any number of ROM sensors 6 may be used. The ROM sensor 6 attached to the patient 46 contains circuitry that relays the position of the ROM sensor 6, and hence the position of the patient's 46 body to which the ROM sensor 6 is attached, in the electromagnetic field 52. The position of the ROM sensor 6 and of the patient 46 are represented through position and angular movements in six degrees of freedom: x, y, z, pitch, roll, and yaw. The ROM sensor 6 operates at a frequency of 100 Hz or more, although any suitable frequency may be used.

A suitable ROM transmitter 50, ROM sensor 6 and ROM signal processing unit 60 is the Nest of Birds™ pulsed DC electromagnetic sensing product available from Ascension Technology Corporation, P.O. Box 527, Burlington, Vt. 05402. The Internet address of Ascension Technologies is www.ascension-tech.com.

Other ROM sensing technologies may be suitable, such as AC electromagnetic sensing or optical sensing. Pulsed DC electromagnetic sensing offers advantages over these technologies. Optical sensing requires that a clear line of sight be maintained, which is not required in magnetic sensing. AC electromagnetic sensing involves a rapidly-fluctuating magnetic field, which induces eddy currents in conductive materials in the electromagnetic field. The eddy currents introduce interference and noise into the data and environment, greatly increasing electromagnetic interference issues with other equipment in the general vicinity of the CNMP. Pulsed DC electromagnetic sensing reduces the problem of eddy currents, although stray magnetic fields and nearby metallic objects can reduce the performance of the pulsed DC system.

As used in this application the term "remote sensing technology" means any technology involving the location of a detector with respect to a source of energy or in an energy field. The term "remote sensing technology" includes pulsed DC electromagnetic sensing, as described above, AC electromagnetic sensing, optical sensing, and any other position sensing technology that involves location of a detector with respect to an energy source or an energy field.

Figure 5:
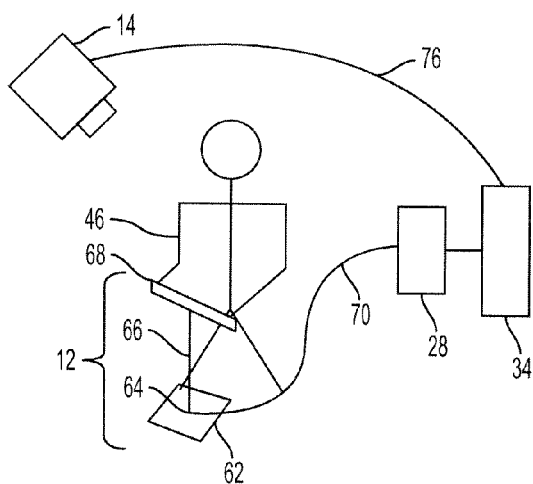
FIG. 5 is a schematic diagram of the collection of isometric function data.

FIG. 5 illustrates the generation of an isometric function signal 24 from a isometric function sensor 12. The isometric function sensor 12 comprises a footplate 62 and a strain gauge 64 mounted on the footplate 62. A cord 66 is attached to strain gauge 64 and a handle 68 is attached to cord 66. The patient 46 stands on the footplate 62 and pulls upward on the handle 68, exerting a force on cord 66 and hence on strain gauge 64. Strain gauge 64 generates a isometric function signal 24 in response to force exerted by patient 46.

A suitable strain gauge 64 is an S-beam load cell, model L2350, from Futek Advanced Sensor Technology ("Futek"), 10 Thomas, Irvine, Calif. 92618. The strain gauge 64 has a rated capacity of 300 pounds of force and can detect increments of 0.3 pounds of force. The isometric function signal 24 varies between −2.5 and +2.5 volts, depending on the force exerted on the strain gauge 64.

Isometric function signal 24 is conveyed by isometric function cable 70 to CNMP housing 28. The isometric function signal 24 is processed to isometric function data within the CNMP housing by a single channel, which operates at 100 Hz or more, but which may be operated at any suitable frequency.

Figure 6:
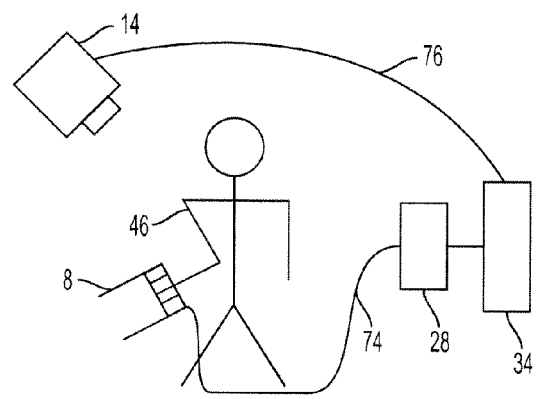
FIG. 6 is a schematic diagram of the collection of grip data.

FIG. 6 illustrates generation of the grip strength signal 20 by the grip strength sensor 8. The patient 46 grips the grip strength sensor 8 in his or her hand and exerts as much gripping force as possible. A pressure transducer within the grip strength sensor 8 generates the grip strength signal 20, which may vary between −2.5 and +2.5 volts, depending on the gripping force exerted by patient 46. The grip strength signal 20 is transmitted through grip sensor cable 74 to the CNMP housing 28. The grip strength signal 20 is converted to grip data within the CNMP housing 28 by a single channel that operates at a frequency of 100 Hz or more, but which may operate at any suitable frequency. A suitable grip strength sensor 8 is the Jamar Grip Strength Gage model 5030PT manufactured by Sammons Preston, Inc. The internet address for Sammons Preston is www.sammonspreston.com.

Figure 7:
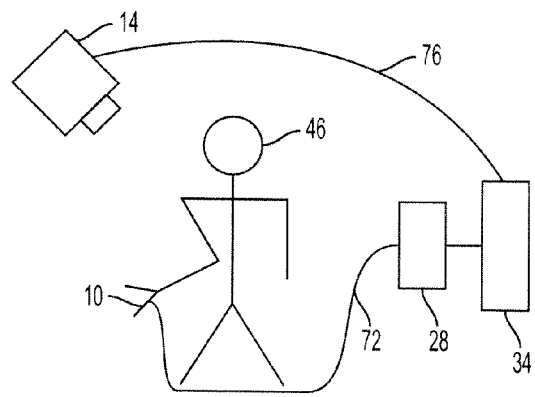
FIG. 7 is a schematic diagram of the collection of pinch data.

FIG. 7 illustrates generation of the pinch strength signal 22 by the pinch strength sensor 10. The patient 46 pinches the pinch strength sensor 10 between a thumb and a finger. The pinch strength sensor 10 generates a pinch strength signal 22 in response to the force applied by the patient 46 to the pinch strength sensor 10. A suitable pinch sensor 10 is model L1020-Q10510 from Futek. The pinch strength signal 22 varies between −2.5 to +2.5 volts, depending on the force exerted on the pinch strength sensor 10 by the patient 46. The pinch strength signal 22 is transmitted through the pinch strength sensor cable 72 to the CNMP housing 28. The pinch strength signal 22 is processed within the CNMP housing 28 by a single channel that operates at a frequency of 100 Hz or more, but which may operate at any suitable frequency.

As shown by FIGS. 3 through 7, video camera 14 records video images of the patient 46 while any or all of EMG sensors 4, ROM sensor 6, grip strength sensor 8, pinch strength sensor 10 or isometric function sensor 12 are in use. The video camera 14 generates video information 26 that is transmitted through video cable 76 to the first client computer 34. The video information 26 is passed into a PCMCIA card acting as a USB hub and is stored for future reference. The video information 26 may be monitored by a healthcare provider during the tests and may be stored as a visual record of the tests.

FIG. 8 illustrates the operations occurring in the CNMP housing 28. ROM signal 18 enters CNMP housing 28 by way of a suitable input jack and is conveyed to ROM signal processing device 60. ROM signal processing device 60 converts ROM signal 18 to ROM data 32, ready for further processing by first client computer 34. As indicated above, a suitable ROM signal processing device 60 is the Nest of Birds™ product by Ascension Technologies Corporation. ROM data 32 is conveyed to a suitable output jack.

Isometric function signal 24, grip signal 20 and pinch signal 22, each appearing as a single channel, enter the CNMP housing 28 through suitable input jacks and are processed by signal conditioning and conversion board 78. Two EMG cable assemblies 48 are connected to the CNMP housing 28 by suitable jack connections, each of the EMG cable assemblies 48 is able to convey nine channels of EMG signal 16 from eighteen separate EMG sensors 4. Each channel of EMG signal 16 is processed by the signal conditioning and conversion board 78. The output of the signal conditioning and conversion board 78 is CNMP data 30 comprising EMG data 82, isometric function data 84, grip data 86 and pinch data 88, all ready for further processing by client computer 34. CNMP data 30 is output at a suitable output jack.

Figure 9:
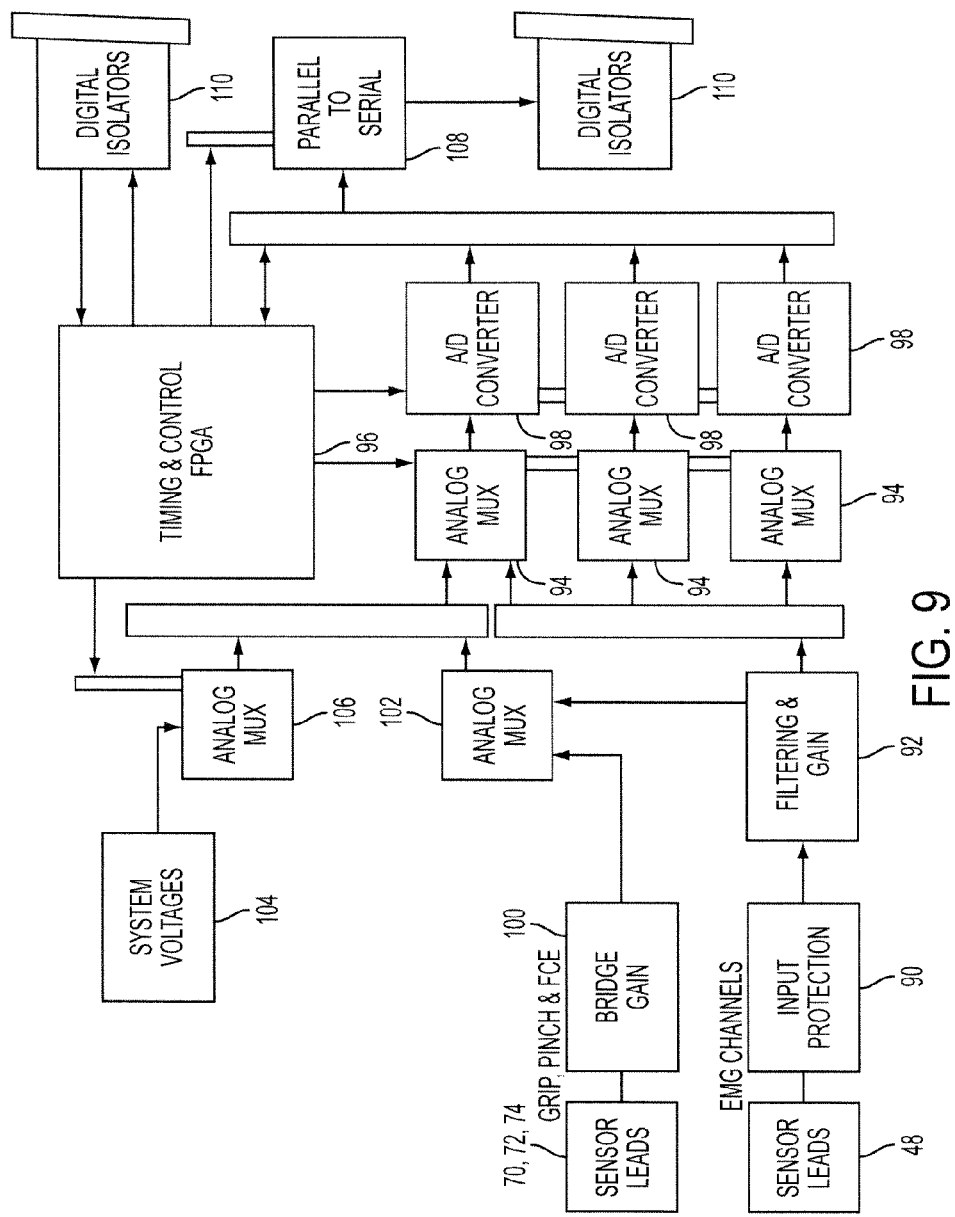
FIG. 9 is a block diagram of the signal conditioning and conversion circuit board.

FIG. 9 illustrates operation of the signal conditioning and conversion board 78. The signal conditioning and conversion board 78 conditions EMG signal 16, isometric function signal 24, pinch signal 22, and grip signal 20 and converts those signals 16, 24, 22, 20 to digital form to be used by the client computer 34 for further processing and analysis.

A shown by FIG. 9, The EMG section of the signal conditioning and conversion board 78 begins with the EMG cable assemblies 48 being fed into an input protection device 90 in order to isolate any high voltage that is potentially dangerous. The resulting signals are sent through an amplification and filtering module 92. The EMG signals 16 are converting to a corresponding voltage, based on the resistance between the EMG sensor 4 pairs. The filtering module 92 provides 60 Hz filtering, with a common mode rejection ratio of 90 dB at a range of 0-100 Hz. The resulting signals are fed through analog multiplexers 94, in order to account for the numerous channels of the surface EMG signal 16. The multiplexers 94 are controlled by a master timing and control mechanism 96, which allows a consistent pass-through of signals through the multiplexer 94 array.

Once the processed EMG signals 16 are passed through the multiplexers 94, the signals 16 are sent through an analog-to-digital converter circuit 98, which changes the EMG signals 16 signals to a digital EMG data 82 in order to prepare the EMG signals 16 for further processing in client computer 34.

The grip, pinch, and functional capacity section of the signal conditioning and conversion board 60 begins with the grip strength sensor cable 74, pinch strength sensor cable 72 and isometric function sensor cable 70 feeding the grip signal 20, pinch signal 22 or isometric function signal 24 into an amplification and bridge gain circuit 100. The differential grip signal 20, pinch signal 22 or isometric function signal 24 is converted into a corresponding voltage. The bridge gain circuit 100 also provides a DC amplification voltage along with an isolated ground component to provide sensor bridge amplification. The resulting processed grip signal 20, pinch signal 22 or isometric function signal 24 is fed through analog multiplexers 102, 94, in order to account for the numerous channels of EMG signal 16. The multiplexers 102, 94 are controlled by a master timing and control mechanism 96, which allows a consistent pass-through of signals through the multiplexer 102, 94 array.

Once the processed grip signal 20, pinch signal 22 or isometric function signal 24 is passed through the multiplexer array 102, 94, the signal is sent through an analog-to-digital converter circuit 98, which changes the grip signal 20, pinch signal 22 or isometric function signal 24 to a digital grip data 86, pinch data 88 or isometric function data 84 in order to prepare the grip signal 20, pinch signal 22 or isometric function signal 24 for further processing by first client computer 34.

The system voltages component 104 of the signal conditioning and conversion board 60 is a stand-alone power supply. The system voltages component 104 operates at a constant voltage of 5 volts at a current of 2 amps. The system voltages component 104 also contains a differential voltage of −12 to +12 volts at an approximate current of 0.4 amps. The resulting signals from the power supply are fed into a multiplexer 106 for distribution in the circuit.

All of the resulting digital EMG data 82, grip data 86, pinch data 88 and isometric function data 84 from the analog-to-digital converters 98 are passed on to a parallel-to-serial converter 108, which prepares the output of the converters 108 to be sent over a standard USB interface to the first client computer 34. The resulting EMG data 82, grip data 86, pinch data 88 and isometric function data 84 are subject to a digital isolation circuit 110, in order to isolate the patient 46 and other participants from the signal conditioning and conversion board 78. The EMG data 82, grip data 86, pinch data 88 and isometric function data 84 are sent from the signal conditioning and conversion board 78 over a USB interface into a USB port on the first client computer 34.

Figure 10:
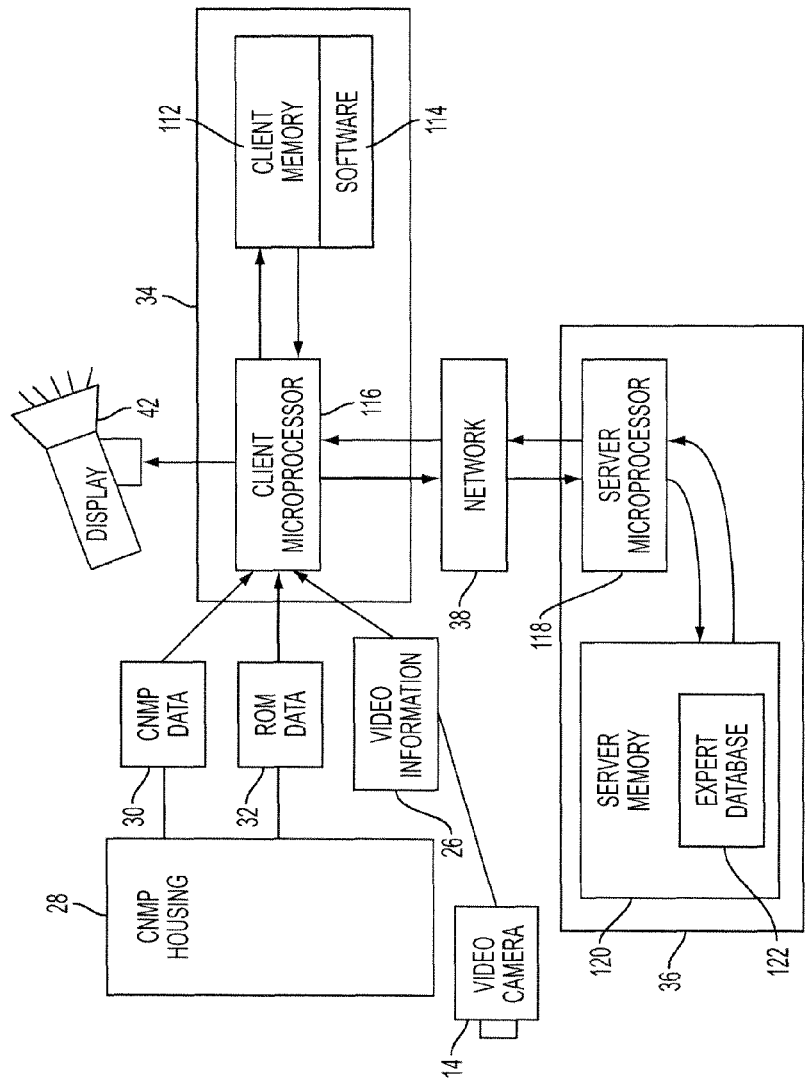
FIG. 10 is a block diagram of information flow through the client computer and server computer.

FIG. 10 illustrates the flow of information from the CNMP housing 28. From the CNMP housing 28, ROM data 32 and CNMP data 30 are fed to first client computer 34. CNMP data 30 comprises EMG data 82, grip data 86, pinch data 88 and isometric function data 84. Video information 26 also is fed to the first client computer 34. First client computer 34 memory 112 contains first client computer software 114 that controls operation of first client computer microprocessor 116. In response to appropriate commands from a user, first client computer microprocessor 116 directs storage of ROM data 32, video information 26 and CNMP data 30 in first client computer memory 112. Instructions and other information are displayed to user by display 42.

On instruction from user, first client computer microprocessor 116 may connect to computer network 38 and negotiate a network connection with server computer 36. First client computer microprocessor 116 may direct that ROM data 32, video information 26 and CNMP data 30 be sent to server computer 36 over computer network 38 in an encrypted format to protect patient information.

Server computer 36 includes server computer microprocessor 118 and server computer memory 120. Server computer memory 120 contains an expert database 122. Server computer microprocessor 118 is programmed to analyze ROM data 32 and CNMP data 30 and to extract patterns from these data. Server computer microprocessor 118 compares the patterns detected to expert database 122 and associates a patient profile 40 with the detected patterns. Server computer 36 may transmit the patient profile 40 to the first client computer 34 over network 38 for display 42 to user. Alternatively, server computer 36 may transmit patient profile 40 over computer network 38 to the second client computer 35 for display to any authorized person, such as an insurer or employer.

FIGS. 11-17 describe the operation of first client computer software 114. The software 114 is resident in the first client computer memory 112 and operates the comprehensive neuromuscular profiler system. In overview, the first client computer software 114 allows a user to select or to enter information about a patient 46 into the first client computer memory 112. The first client computer software 114 allows the user to select among several different protocols for tests to be administered to a patient 46. Each protocol is designed to collect information about the functioning of a particular portion of the patient's 46 body. The first client computer software 114 allows first client computer 34 to display to the user or to the patient 46 information about a selected protocol, including which of the EMG sensors 4, ROM sensor 6, isometric function sensor 12, grip strength sensor 8 or pinch strength sensor 10 should be used during each portion of the protocol. The first client computer software 114 may instruct the user as to the correct location and placement of the EMG sensors 4 and ROM sensor 6. The first client computer software 114 may instruct the patient as to the correct performance of each task in the selected protocol.

The first client computer software 114 oversees collection of the appropriate EMG data 82, ROM data 32, grip data 86, pinch data 88 and isometric function data 84 and also oversees recording of video information 26. The first client computer software 114 allows first client computer 34 to transmit CNMP data 30, ROM data 32 and video information 30 to a server computer 36 over computer network 38. The first client computer software may allow first client computer to receive the patient profile 40 from the server computer 36 after completion of the analysis by the server computer 36.

Each of the above steps relating to the first client computer software 114 is described in more detail in the following paragraphs.

A first client computer 34 running the client computer software 114 displays a 'main' screen 124 to a user. The user is a technician who administers the test protocols to the patient 46. The user is presented with several options on the Main screen 124, and the user may select any of the options using any of the techniques that are well known in the art.

Figure 11:
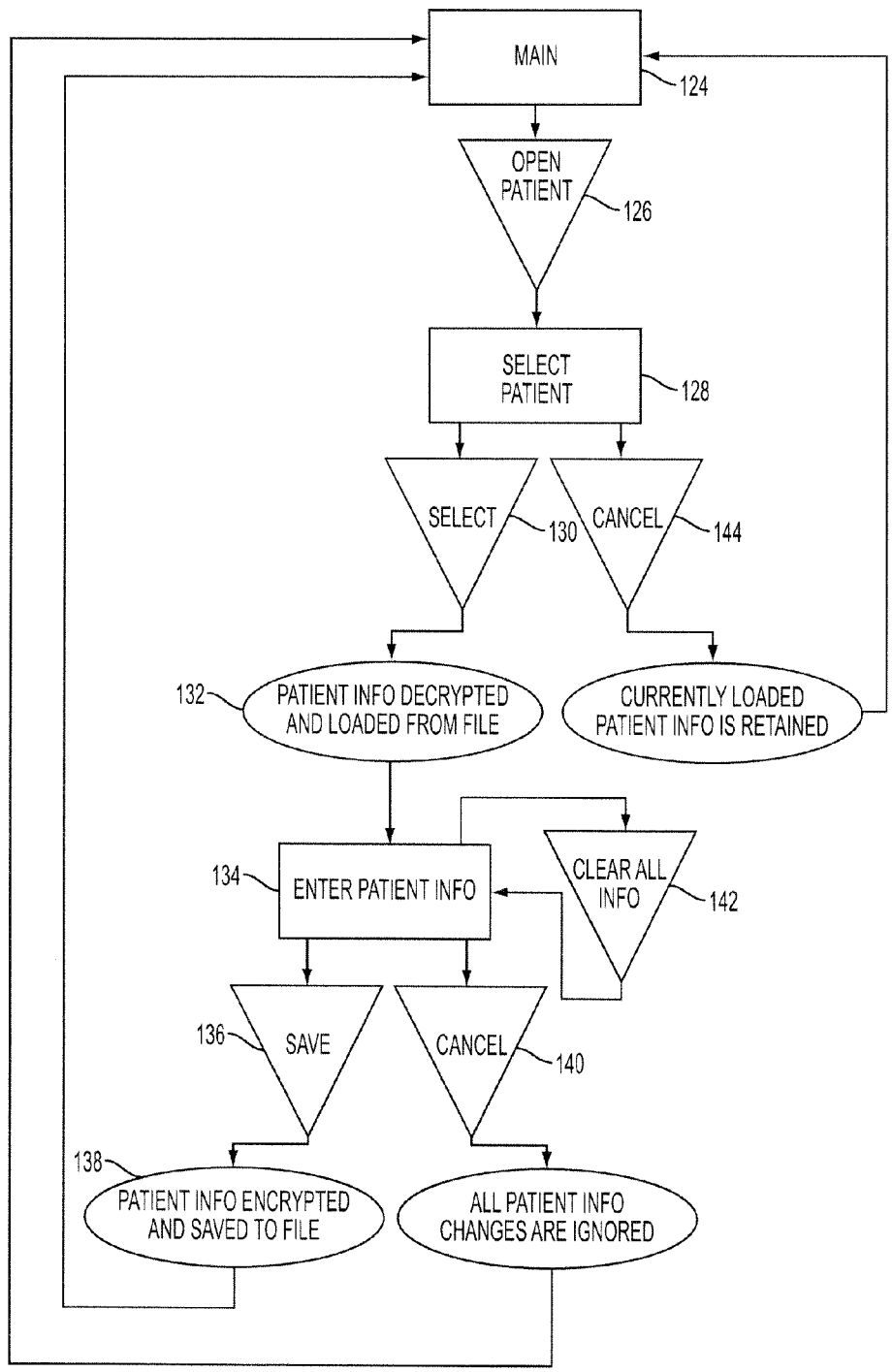
FIG. 11 is a flowchart of the select patient function of the client computer software.

As shown by FIG. 11, from the Main screen 124 the user may select the "open patient" option 126. The user is presented with a select patient screen 128 that allows the user to select the identity of the patient 46 (either by name or by some other unique identifier) from a list of patient 46 identities. Patient 46 information includes identifying information for the patient 46 and such other information as is deemed necessary, which may include insurance information, diagnosis information, prior test results, and any other information that may be desirable. Patient 46 information is stored in encrypted form on the first client computer memory 112. The user selects 130 one of the unique patient identifiers and the patient 46 information for that patient 46 is decrypted and displayed 132 to the user in one or more screens. The user then may edit or add to the patient information 134, including performing additional protocols as described below. After the entry of new patient information is completed, the user may elect to save 136 the new patient information, in which case the patient information is encrypted and saved 138 to the hard disk. Alternately, the user may elect to cancel 140 the entry of patient information at any time and return to the Main menu. The user also may clear patient information 142 entered without returning to the main menu. The user may elect to cancel opening of a patient file 144, in which case existing patient files are not amended.

Figure 12:
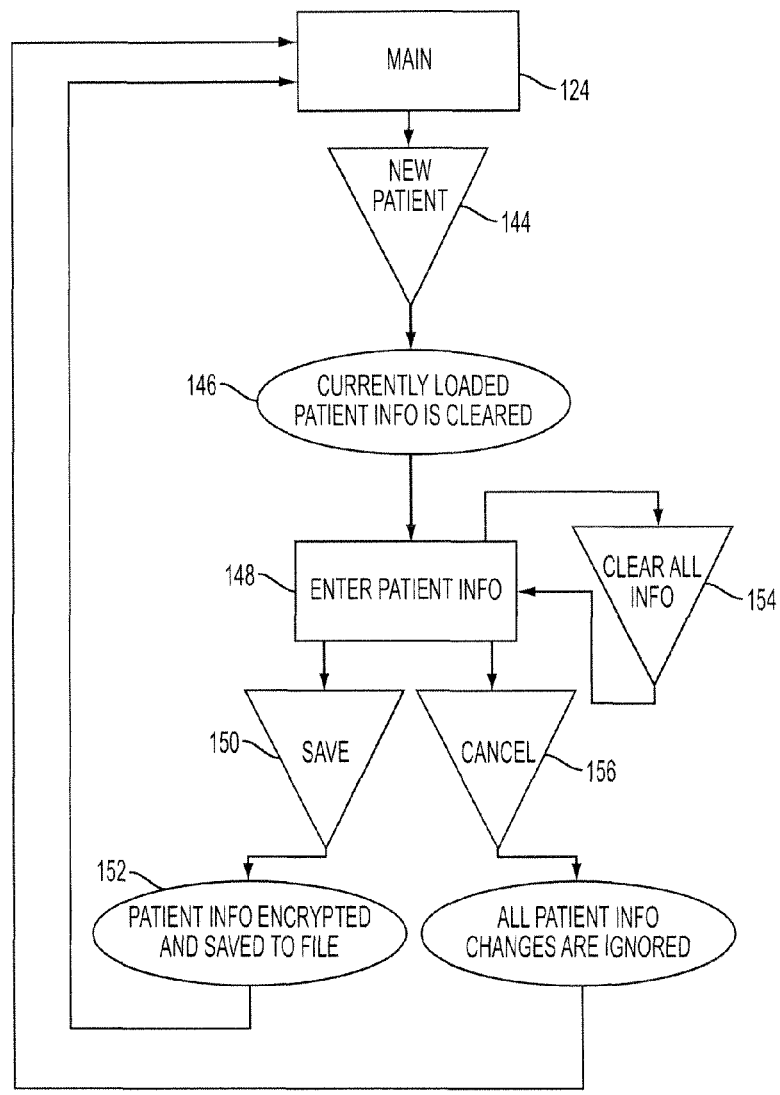
FIG. 12 is a flowchart of the new patient function of the client computer software.

As shown by FIG. 12, the user may enter information concerning a new patient for whom no file is saved within the, computer system. From the Main menu 124, the user selects "new patient" 144. The user is presented with patient information screens with the fields blank 146. The user then enters information into the blank fields, as appropriate 148. The information entered may include new protocol data derived from the administration of a protocol to the patient, as discussed below. Once the entry of the new patient information 148 is complete, the user may elect to save the information 150. The information is then encrypted and saved to the hard disk drive 152 of the first client computer 34. The user also may elect to clear the new patient information 154 or to cancel the operation 156 and return to the main screen.

Figure 13:
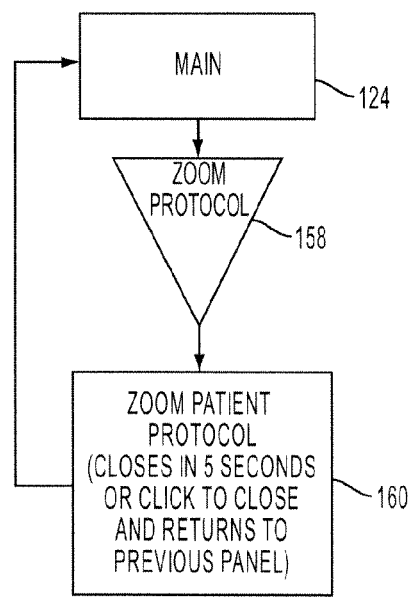
FIG. 13 is a flowchart of the zoom patient protocol function of the client computer software.

FIG. 13 shows the "Zoom patient protocol" option presented to the user by the Main menu 124. As used in this application, the term "zoom" means to selectably enlarge an image on the display screen. For the "zoom patient protocol," the user is presented with an image of a region on the human body. The user selects 158 the region of the human body corresponding to the protocol to be administered to the patient. The image of the body region selected "zooms" 160; that is, enlarges, on the display monitor 42. The proper location of the EMG sensor 4 locations for the selected patient protocol are illustrated on the enlarged image of the body and a list of the muscles to be monitored is displayed to the user.

Eight different protocols are available to the user, and hence eight different locations may be "zoomed" 160. Those protocols are as follows: Cervical, Thoracic, Lumbosacral, Carpal Tunnel, Shoulder, Lower Extremities, Custom Ankle, and Hip & Groin. Each of the protocols provide EMG sensor 4 locations for the left and the right sides of the patient's 46 body, resulting in a total of sixteen different sets of EMG sensor locations 44. The appropriate EMG sensor locations 44 for the eight protocols are contained in Table 1.

TABLE 1

ELECTRODE PLACEMENTS

CERVICAL PROTOCOL

| RIGHT | | LEFT | |
|---|---|---|---|
| CH1: | Right Sternocleidomastoid | CH10: | Left Sternocleidomastoid |
| CH2: | Right Scalene | CH11: | Left Scalene |
| CH3: | Right Paracervical | CH12: | Left Paracervical |
| CH4: | Right Upper Trapezius | CH13: | Left Upper Trapezius |

THORACIC PROTOCOL

| RIGHT | | LEFT | |
|---|---|---|---|
| CH1: | Right Middle Trapezius | CH10: | Left Middle Trapezius |
| CH2: | Right Lower Trapezius | CH11: | Left Lower Trapezius |
| CH3: | Right Paraspinal T5-T8 | CH12: | Left Paraspinal T5-T8 |
| CH4: | Right Paraspinal T8-T12 | CH13: | Left Paraspinal T8-T12 |
| CH5: | Right Latissimus Dorsi | CH14: | Left Latissimus Dorsi |
| CH6: | Right Serratus Posterior Inferior | CH15: | Left Serratus Posterior Inferior |

LUMBOSACRAL PROTOCOL

| RIGHT | | LEFT | |
|---|---|---|---|
| CH1: | Right Paraspinal L1-L3 | CH10: | Left Paraspinal L1-L3 |
| CH2: | Right Paraspinal L5-S1 | CH11: | Left Paraspinal L5-S1 |
| CH3: | Right Quadratus Lumborum | CH12: | Left Quadratus Lumborum |
| CH4: | Right Gluteus Maximus | CH13: | Left Gluteus Maximus |
| CH5: | Right Rectus Abdominis | CH14: | Left Rectus Abdominis |
| CH6: | Right Abdominal Oblique | CH15: | Left Abdominal Oblique |
| CH7: | Right Hamstring | CH16: | Left Hamstring |

TABLE 1-continued

ELECTRODE PLACEMENTS

CARPAL TUNNEL PROTOCOL

| RIGHT | | LEFT | |
|---|---|---|---|
| CH1: | Right Sternocleidomastoid | CH10: | Left Sternocleidomastoid |
| CH2: | Right Scalene | CH11: | Left Scalene |
| CH3: | Right Paracervical | CH12: | Left Paracervical |
| CH4: | Right Upper Trapezius | CH13: | Left Upper Trapezius |
| CH5: | Right Deltoid | CH14: | Left Deltoid |
| CH6: | Right Biceps | CH15: | Left Biceps |
| CH7: | Right Triceps | CH16: | Left Triceps |
| CH8: | Right Wrist Flexor/Extensor | CH17: | Left Wrist Flexor/Extensor |
| CH9: | Right Thenar/Palmer | CH18: | Left Thenar/Palmer |

SHOULDER PROTOCOL

| RIGHT | | LEFT | |
|---|---|---|---|
| CH1: | Right Scalene | CH10: | Left Scalene |
| CH2: | Right Paracervical | CH11: | Left Paracervical |
| CH3: | Right Upper Trapezius | CH12: | Left Upper Trapezius |
| CH4: | Right Pectoralis Major | CH13: | Left Pectoralis Major |
| CH5: | Right Supraspinatus | CH14: | Left Supraspinatus |
| CH6: | Right Teres Major | CH15: | Left Teres Major |
| CH7: | Right Latissimus Dorsi | CH16: | Left Latissimus Dorsi |
| CH8: | Right Deltoid | CH17: | Left Deltoid |
| CH9: | Right Biceps | CH18: | Left Biceps |

LOWER EXTREMITIES PROTOCOL

| RIGHT | | LEFT | |
|---|---|---|---|
| CH1: | Right Quadriceps | CH10: | Left Quadriceps |
| CH2: | Right Hamstring | CH11: | Left Hamstring |
| CH3: | Right Tibialis Anterior | CH12: | Left Tibialis Anterior |
| CH4: | Right Gastrocnemius | CH13: | Left Gastrocnemius |

TABLE 1-continued

ELECTRODE PLACEMENTS

CUSTOM ANKLE PROTOCOL

| RIGHT | | LEFT | |
|---|---|---|---|
| CH1: | Right Tibialis Anterior | CH10: | Left Tibialis Anterior |
| CH2: | Right Gastrocnemius | CH11: | Left Gastrocnemius |
| CH3: | Right Lateral Ankle | CH12: | Left Lateral Ankle |
| CH4: | Right Medial Ankle | CH13: | Left Medial Ankle |

HIP & GROIN PROTOCOL

| RIGHT | | LEFT | |
|---|---|---|---|
| CH1: | Right Paraspinal L5-S1 | CH10: | Left Paraspinal L5-S1 |
| CH2: | Right Gluteus Maximus | CH11: | Left Gluteus Maximus |
| CH3: | Right Iliopsoas | CH12: | Left Iliopsoas |
| CH4: | Right Rectus Abdominus | CH13: | Left Rectus Abdominus |
| CH5: | Right Abdominal Oblique | CH14: | Left Abdominal Oblique |
| CH6: | Right Gracilis | CH15: | Left Gracilis |
| CH7: | Right Hamstrings | CH16: | Left Hamstrings |

The EMG sensors 4 are attached to the patient in a conventional manner for use of EMG technology. Conventional connection requires that a patient 46 ground be established with one EMG sensor 4 as a reference and that two EMG sensors 4 be attached to each muscle to be evaluated. The data collected by the two EMG sensors 4 represents a difference in electrical potential between the two EMG sensors 4 connected to each muscle.

Each protocol also involves the use of a remote tracking device (ROM sensor 6). The ROM sensor 6 is attached to the body of the patient 46 at the location specified by Table 2. The ROM sensor 6 is attached by an elastic bandage, by a strap, by incorporating the ROM sensor 6 into an article of clothing, by an adhesive or by any other suitable means.

TABLE 2

| Protocol | Motion detector location |
|---|---|
| Cervical Protocol | Back of the head |
| Thoracic Protocol | Vicinity of T4-T5 vertebrae |
| Lumbosacral Protocol | Top of the Head |
| Carpal Tunnel Protocol | Hand or Wrist |
| Shoulder Protocol | Back of the head |
| Lower Extremities Protocol | Knee Cap |
| Custom Ankle Protocol | Ankle or Foot |
| Hip & Groin Protocol | Top of the Quadriceps Femoris |

The "zoom patient protocol" screens of FIG. 13 are useful for user training and as a check to the user concerning EMG sensor 4 placement. It is anticipated that as a user becomes facile with the operation of the apparatus that the user will not require instruction by the "zoom patient protocol" 158, 160.

Figure 14:
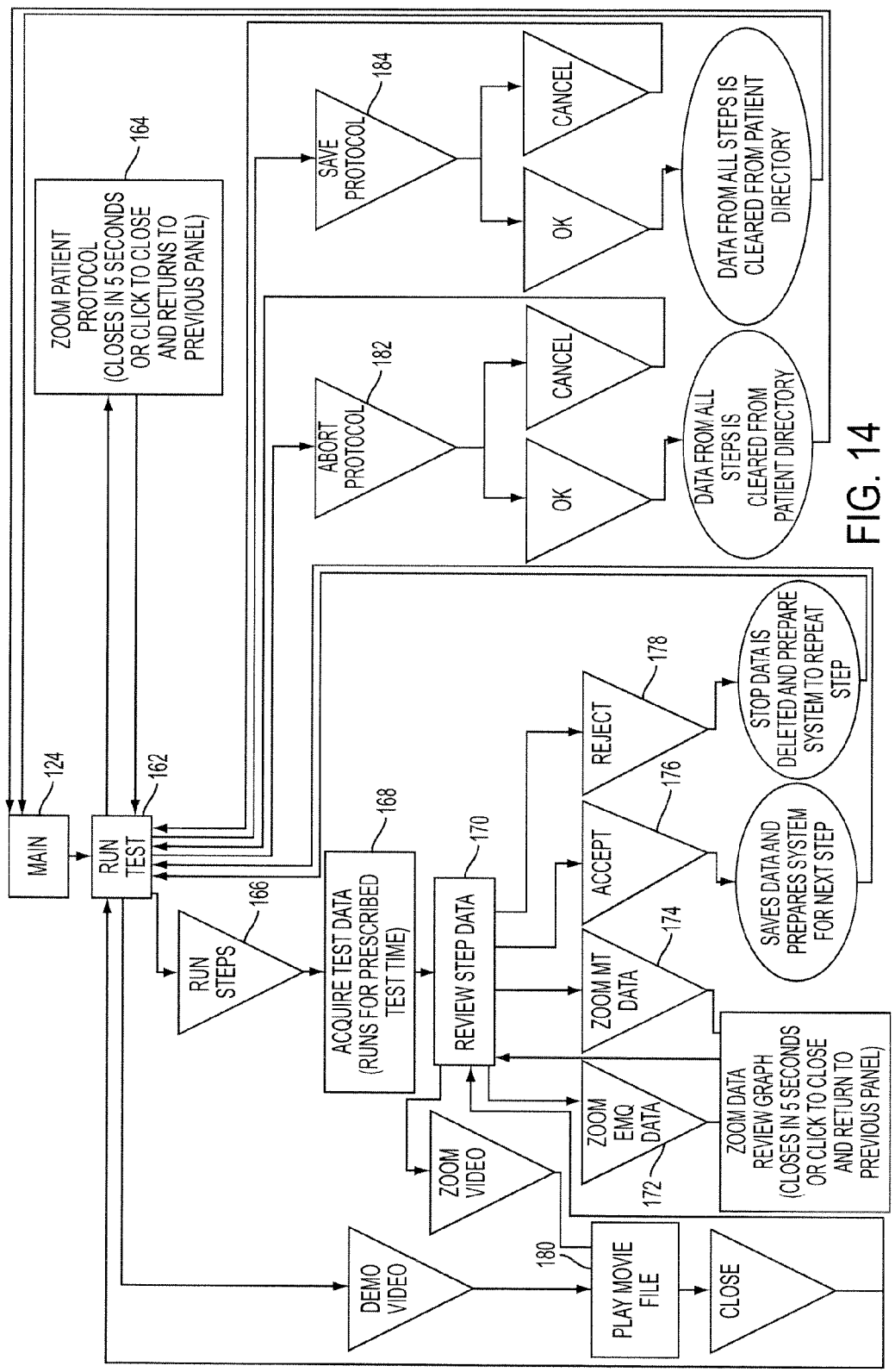
FIG. 14 is a flowchart of the run test function of the client computer software.

FIG. 14 illustrates the use of the first client computer software 114 to perform a protocol and record the results of the protocol. From the Main menu 124, the user elects to run a protocol 162 and selects the protocol that will be run. The cervical protocol is the default if no other protocol is selected.

The user is unable to select the "run test" 162 command unless a new or existing patient file 136, 150 has been loaded. The user may elect to "zoom patient protocol" 164, as described above, to see an illustration of proper EMG sensor 4 placement and a list of muscles to be monitored.

The user will then administer the protocol 166 to the patient. Each protocol comprises several steps. Each protocol includes tests requiring that the patient 46 be connected to a plurality of EMG sensors 4 and to an ROM sensor 6 that are in turn connected to the CNMP housing 28 through EMG sensor cables 48 and a ROM sensor cable 58. Some of the protocols also involve the patient 46 exerting force against an isometric function sensor 12, a grip strength sensor 8, or a finger pinch sensor 10, each of which is connected to the CNMP housing 28. The patient 46 follows instructions by the user or as instructed by the software as the patient 46 performs several tasks. The instructions are displayed to the user and the user verbally instructs the patient 46 to perform the task. Alternatively, the instructions may be displayed to the user on, for example, a computer monitor 42. The tasks are designed to challenge specific muscles to allow measurement of the electrical characteristics of the muscles as they are challenged. Each of the tasks are timed and the patient 46 is allowed fifteen seconds to complete each task.

The first client computer 34 records data as the tests are administered 168. EMG data 82 of the monitored muscles is recorded continuously. The ROM data 32 is collected during the time that the patient 46 is performing a task relating to motion of a body part of the patient 46. The patient 46 is recorded by video camera 14 to create a video record of patient 46 compliance and to allow monitoring by a health care professional. The user also monitors patient 46 compliance and proper performance of the test by the patient 46.

The sequential instructions and challenges to the patient 46 for each step of each protocol is provided below. The protocol instructions below also include instructions to the user to connect or disconnect the isometric function sensor 12 (also referred to as the 'IFT'), the grip sensor 8 and the finger pinch sensor 10, as appropriate for the particular protocol being administered. The ROM sensor 6 is referred to as the "motion tracking device" in the descriptions below. The patient 46 is provided a rest period of fifteen seconds between each of the protocol steps listed below.

Cervical Protocol
a. (flexion/extension) "Slowly bend your head at a constant speed in an arc such that you bend forward to look at the floor and then sweep it backwards such that you are looking at the ceiling. Repeat three times, pausing for two seconds between each repetition."
b. (rotation) "Slowly turn your head at a constant speed to the right, back to center and then to the left. Repeat three times, pausing for two seconds between each repetition."
c. (lateral bending) "Slowly and at a constant speed with your gaze fixed on the wall straight ahead at eye level, try to bring your right ear to your right shoulder, then sweep back through the center to try to bring your left ear to your left shoulder without moving anything but your head. Repeat three times, pausing for two seconds between each repetition."

Thoracic Protocol
a. (Flexion/extension) "Slowly bend forward at the waist at a constant speed while keeping your legs straight, then return to center and then bend backwards and return to center. Repeat three times, pausing for two seconds between each repetition."
b. (Rotation) "Bend over at the waist such that your upper body and lower body are at a 90 degree angle and cross your arms over your chest. Slowly and at a constant speed, twist your upper body to the right, return to center, then twist to the left and return to center. Repeat three times, pausing for two seconds between each repetition"
c. (Lateral Bending) "Stand upright at rest with your gaze fixed on the wall straight ahead at eye level with your arms hanging straight down at your sides. Slowly and at a constant speed, lean to your right and slide your right hand down your right leg, return to rest and then lean to your left and slide your left hand down your left leg and return to rest. Repeat three times, pausing for two seconds between each repetition."
d. (Rowing) "Stand upright with your arms straight out from your body at shoulder level while looking straight forward with your gaze fixed on a spot on the wall at eye level. Slowly and at a constant speed, pull each hand to its respected shoulder by bending your elbows, then return to full extension. Repeat three times, pausing for two seconds between each repetition."
e. (Abduction/Adduction) "Stand upright with your arms relaxed at your sides while looking straight forward with your gaze fixed on a spot on the wall at eye level. Slowly and at a constant speed while keeping your elbows locked, lift your arms sideways from your body over your head and then bring them down again to your sides. Repeat three times pausing, for two seconds between each repetition."
f. (Upright Rowing) "Stand upright with your arms relaxed at your sides while looking straight forward with your gaze fixed on a spot on the wall at eye level. Slowly and at a constant speed, simulate pulling a bar up with both hands to your chin by bending your elbows. Repeat three times, pausing for two seconds between each repetition."

Lumbosacral Protocol
a. (Flexion/Extension) "Slowly bend forward at the waist at a constant speed while keeping your legs straight, then return to center and then bend backwards and return to center. Repeat three times, pausing for two seconds between each repetition."
b. (Rotation) "Stand upright with your arms relaxed at your sides while looking straight forward with your gaze fixed on a spot on the wall at eye level. Slowly and at a constant speed, twist your upper body to the right, back to center, to the left and return to center. Repeat three times, pausing for two seconds between each repetition."
c. (Lateral Bending) "Stand upright at rest with your gaze fixed on the wall staight ahead at eye level with your arms hanging straight down at your sides. Slowly and at a constant speed, lean to your right and slide your right hand down your right leg, return to rest and then lean to your left and slide your left hand down your left leg and return to rest. Repeat three times, pausing for two seconds between each repetition."
d. (IFT Underhand Lifting) "Place your feet on either side of the [IFT] bar at shoulder width while gripping the handle UNDERHANDED with the handle held a few inches above your knees. While keeping your arms straight and knees bent, straighten your legs to lift up on the bar as hard as you can and then return to rest. Repeat three times, pausing for two seconds between each repetition."
e. (IFT Overhand Lifting) "Place your feet on either side of the bar at shoulder width while gripping the handle OVERHANDED with the handle held a few inches above your knees. While keeping your arms straight and knees bent, straighten your legs to lift up on the bar as hard as you can and then return to rest. Repeat three times, pausing for two seconds between each repetition."

Carpal Tunnel Protocol
a. (Flexion/Extension) "Slowly bend your head at a constant speed in an arc such that you bend forward to look at the floor and then sweep it backwards such that you are looking at the ceiling. Repeat three times."
b. (Rotation) "Slowly turn your head at a constant speed to the right, back to center and then to the left. Repeat three times, pausing for two seconds between each repetition."
c. (Lateral Bending) "Slowly and at a constant speed with your gaze fixed on the wall straight ahead at eye level, try to bring your right ear to your right shoulder, then sweep back through the center to try to bring your left ear to your left shoulder without moving anything but your head. Repeat three times, pausing for two seconds between each repetition."

Rest Standing "Stand upright with your arms relaxed at your sides while looking straight forward with your gaze fixed on a spot on the wall at eye level."

d. (System Check) "Ensure the Motion Tracking Device is installed on the back of the patient's RIGHT hand."
e. (Wrist Extension RIGHT) "Bring your RIGHT arm straight out in front of your body at shoulder level and slowly and at a constant speed bend the wrist up and then return it to rest. Repeat three times, pausing for two seconds between each repetition."
f. (Wrist Flexion/Finger Grasp RIGHT) "Bring your RIGHT arm straight out in front of your body at shoulder level with your fingers spread and bend your wrist down and then close your fingers and make a fist, then relax your fingers and return your wrist to rest. Repeat three times, pausing for two seconds between each repetition."
g. (System check) "Ensure the Motion Tracking Device is installed on the back of the patient's LEFT hand."
h. (Wrist Extension LEFT) "Bring your LEFT arm straight out in front of your body at shoulder level and slowly and at a constant speed bend the wrist up and then return it to rest. Repeat three times, pausing for two seconds between each repetition."
i. (Wrist Flexion/Finger Grasp LEFT) "Bring your LEFT arm straight out in front of your body at shoulder level with your fingers spread and bend your wrist down and then close your fingers and make a fist, then relax your fingers and return your wrist to rest. Repeat three times, pausing for two seconds between each repetition."
j. (IFT Installation) "Place the IFT plate on the floor and adjust the strap length as dictated by the protocol."
k. (IFT Underhand Lifting) "Place your feet on either side of the bar at shoulder width while gripping the handle UNDERHANDED with the handle held a few inches above your knees. While keeping your arms straight and knees bent, straighten your legs to lift up on the bar as hard as you can and then return to rest. Repeat three times, pausing for two seconds between each repetition."
l. (IFT Overhand Lifting) "Place your feet on either side of the bar at shoulder width while gripping the handle OVERHANDED with the handle held a few inches above your knees. While keeping your arms straight and knees bent, straighten your legs to lift up on the bar as hard as you can and then return to rest. Repeat three times, pausing for two seconds between each repetition."
m. (Jamar grip installation) "Give the patient the Jamar Grip Device to hold in their right hand."
n. (Grip RIGHT) "Hold the Jamar Grip Device in your RIGHT hand with your arm at your side and lift it with a slightly bent elbow to waist level with your wrist held staight and grip/squeeze the Jamar as hard as you can, then release and return your arm to your side. Repeat three times, pausing for two seconds between each repetition."
o. (Grip LEFT) "Hold the Jamar Grip Device in your LEFT hand with your arm at your side and lift it with a slightly bent elbow to waist level with your wrist held staight and grip/squeeze the Jamar as hard as you can, then release and return your arm to your side. Repeat three times, pausing for two seconds between each repetition."
p. (Pinch Device Installation) "Take the Jamar Grip Device from the patient and give them the Pinch Sensor Device to hold in their right hand."
q. (Pinch RIGHT) "Hold the pinch sensor in your RIGHT hand between your thumb and index finger with your arm at your side and squeeze the sensor as hard as you can. Repeat three times, pausing for two seconds between each repetition."
r. (Pinch LEFT) "Hold the pinch sensor in your LEFT hand between your thumb and index finger with your arm at your side and squeeze the sensor as hard as you can. Repeat three times, pausing for two seconds between each repetition."

Shoulder
a. (Flexion/Extension) "Slowly bend your head at a constant speed in an arc such that you bend forward to look at the floor and then sweep it backwards such that you are looking at the ceiling. Repeat three times, pausing for two seconds between each repetition."
b. (Rotation) "Slowly turn your head at a constant speed to the right, back to center and then to the left. Repeat three times, pausing for two seconds between each repetition."
c. (Lateral Bending) "Slowly and at a constant speed with your gaze fixed on the wall straight ahead at eye level, try to bring your right ear to your right shoulder, then sweep back through the center to try to bring your left ear to your left shoulder without moving anything but your head. Repeat three times, pausing for two seconds between each repetition."
d. (Shoulder Shrug) "Standing in an upright position with your arms at your sides, elevate your shoulders towards your ears and hold for approximately two seconds and then return to rest. Repeat three times."
e. (Abduction/Adduction) "Stand upright with your arms relaxed at your sides while looking straight forward with your gaze fixed on a spot on the wall at eye level. Slowly and at a constant speed while keeping your elbows locked, lift your arms sideways from your body over your head and then bring them down again to your sides. Repeat three times pausing, for two seconds between each repetition."
f. (Interior/Exterior Rotation) "While standing upright with your arms at your side with the elbows locked at 90 degrees; slowly and at a constant speed bring your hands up towards and past your ears and then bring them back down and to the back as far as possible then return to rest. Repeat three times, pausing for two seconds between each repetition."
g. (IFT Installation) "Place the IFT plate on the floor and adjust the strap length as dictated by the protocol."
h. (IFT Underhand Lifting) "Place your feet on either side of the bar at shoulder width while gripping the handle UNDERHANDED with the handle held a few inches above your knees. While keeping your arms straight and knees bent, straighten your legs to lift up on the bar as hard as you can and then return to rest. Repeat three times, pausing for two seconds between each repetition."
i. (IFT Overhand Lifting) "Place your feet on either side of the bar at shoulder width while gripping the handle OVERHANDED with the handle held a few inches above your knees. While keeping your arms straight and knees bent, straighten your legs to lift up on the bar as hard as you can and then return to rest. Repeat three times, pausing for two seconds between each repetition."

Lower Extremities Protocol a. (Walking) "Take 3 steps forward and then 3 steps backwards to return to the original position. Repeat three times, pausing for two seconds between each repetition."
b. (Walking) "Take 3 steps forward and then 3 steps backwards to return to the original position. Repeat three times, pausing for two seconds between each repetition."
c. (Knee Flexion/Extension RIGHT) "While supporting yourself on a stationary object, raise your RIGHT leg straight forward in front of your body and then bend the knee, straighten your leg again and then return to a standing position. Repeat three times, pausing for two seconds between each repetition."
d. (Knee Flexion/Extension LEFT) "While supporting yourself on a stationary object, raise your LEFT leg straight forward in front of your body and then bend the knee, straighten your leg again and then return to a standing position. Repeat three times, pausing for two seconds between each repetition."
e. (Deep Knee Bends) "While supporting yourself on a stationary object, perform a deep knee bend while ensuring that your legs never exceed a maximum angle of 90 degrees to one another. Repeat three times, pausing for two seconds between each repetition."Custom Ankle Protocol
a. (Walking) "Take 3 steps forward and then 3 steps backwards to return to the original position. Repeat three times, pausing for two seconds between each repetition."
b. (Walking) "Take 3 steps forward and then 3 steps backwards to return to the original position. Repeat three times, pausing for two seconds between each repetition."
c. (Ankle Flexion/Extension RIGHT) "While supporting yourself on a stationary object while keeping your LEFT leg straight, lift your RIGHT leg by bending at the knee and bend your ankle slowly and at a constant speed such that your toes point down, center and then up and back to center. Repeat three times, pausing for two seconds between each repetition."
d. (Ankle Rotation RIGHT) "While supporting yourself on a stationary object while keeping your LEFT leg straight, lift your RIGHT leg by bending at the knee and rotate your ankle slowly and at a constant speed to the right, back to center, back to left and finally returning to center. Repeat three times, pausing for two seconds between each repetition."
e. (Ankle Flexion/Extension LEFT) "While supporting yourself on a stationary object while keeping your RIGHT leg straight, lift your LEFT leg by bending at the knee and bend your ankle slowly and at a constant speed such that your toes point down, center and then up and back to center. Repeat three times, pausing for two seconds between each repetition."
f. (Ankle Rotation LEFT) "While supporting yourself on a stationary object while keeping your RIGHT leg straight, lift your LEFT leg by bending at the knee and rotate your ankle slowly and at a constant speed to the right, back to center, back to left and finally returning to center. Repeat three times, pausing for two seconds between each repetition."

Hip & Groin Protocol a. (Flexion/Extension RIGHT) "While supporting yourself on a stationary object while keeping your RIGHT leg straight with the toes pointed upwards, slowly and at a constant speed raise your leg forward as high as possible, back to rest and then backwards as high as possible and then return to rest. Repeat three times, pausing for two seconds between each repetition."
b. (Abduction/Adduction RIGHT) "While supporting yourself on a stationary object and keeping your RIGHT leg straight with the toes pointed upwards swing your leg inwards to the left as far as possible, back to center and then as far right as possible and return to rest. Repeat three times, pausing for two seconds between each repetition."
c. (Flexion/Extension LEFT) "While supporting yourself on a stationary object while keeping your LEFT leg straight with the toes pointed upwards, slowly and at a constant speed raise your leg forward as high as possible, back to rest and then backwards as high as possible and then return to rest. Repeat three times, pausing for two seconds between each repetition."
d. (Abduction/Adduction LEFT) "While supporting yourself on a stationary object and keeping your LEFT leg straight with the toes pointed upwards swing your leg inwards to the right as far as possible, back to center and then as far left as possible and return to rest. Repeat three times, pausing for two seconds between each repetition."
e. (Deep Knee Bends) "While supporting yourself on a stationary object, perform a deep knee bend while ensuring that your legs never exceed a maximum angle of 90 degrees to one another. Repeat three times, pausing for two seconds between each repetition."

Upon completion of each step of the selected protocol, the user may review graphs of the data collected to determine that the CNMP apparatus 2 and the patient performed the step properly and that the data was properly recorded. In the 'review step data,' screen 170, the user is presented with small images of data graphs for the ROM data 32 and the EMG data 82 collected. The user may "zoom" (enlarge) 172, 174 the data graphs to verify the proper conduct of the step. On the 'review step data' screen 170, the user also is presented with a small image of the collected video information 26, which can also be zoomed for closer examination. If the user is satisfied that the data was properly collected and the test properly run, the user may accept and save the data 176. If the user detects an error in the data, for example a failure of an EMG sensor 4 or failure of the patient 46 to comply fully with the instructions, the user may reject 178 the data and request that the patient 46 repeat the step. The user may 'zoom' a demonstration video file 180 for display to the patient 46 to show the patient 46 the actions that the patient 46 will perform in the step.

The user may abort the protocol 182, deleting all collected data. The user also may save the protocol 184, which 'zips' (compresses) the CNMP data 30 and ROM data 32 to create a smaller data file for transmission over a network 38 to a server computer 36.

Figure 15:
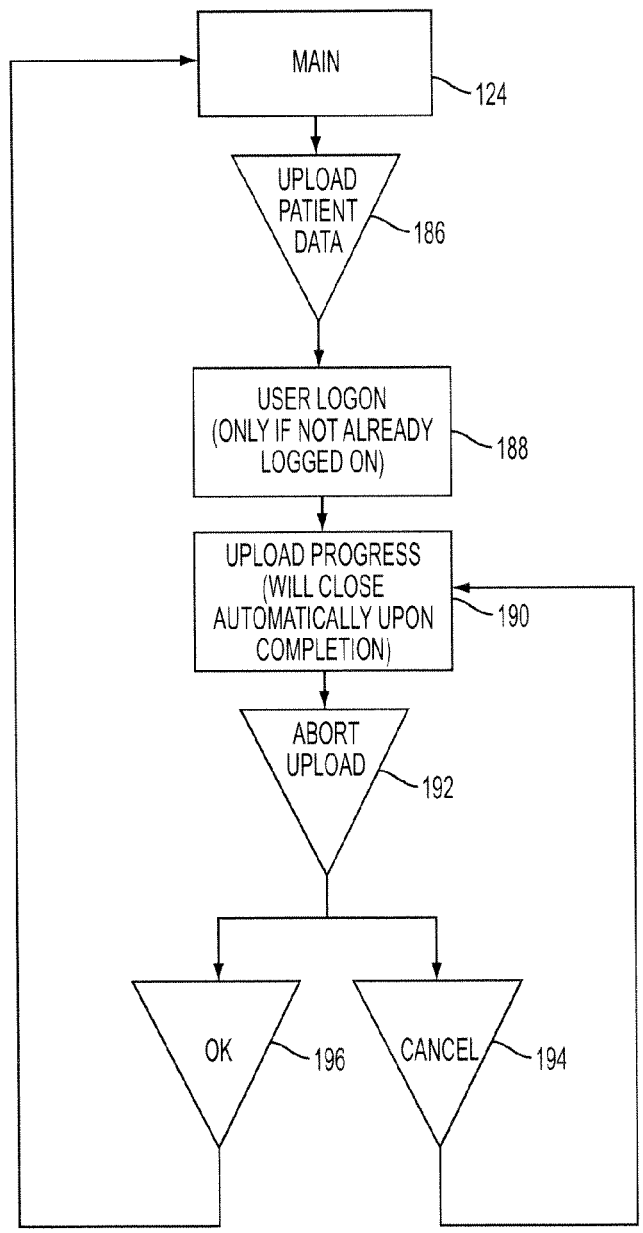
FIG. 15 is a flowchart of the upload data function of the client computer software.

FIG. 15 illustrates the upload process for transferring the CNMP data 30, ROM data 30 and video information 26 to a server computer 36 for analysis. From the 'Main' screen 124, patient data is uploaded 186. The user logs onto the network 188, assuring the server computer 36 that user is authorized to access server computer 36. The user instructs the client computer 34 to upload the data to the server computer 36 and the data is transferred 190. The user may instruct the client computer 34 to abort 192 the upload process and is provided an opportunity to ok 196 or cancel 194 the abort command. If the upload is aborted 196, the user is returned to the main screen 124.

Figure 16:
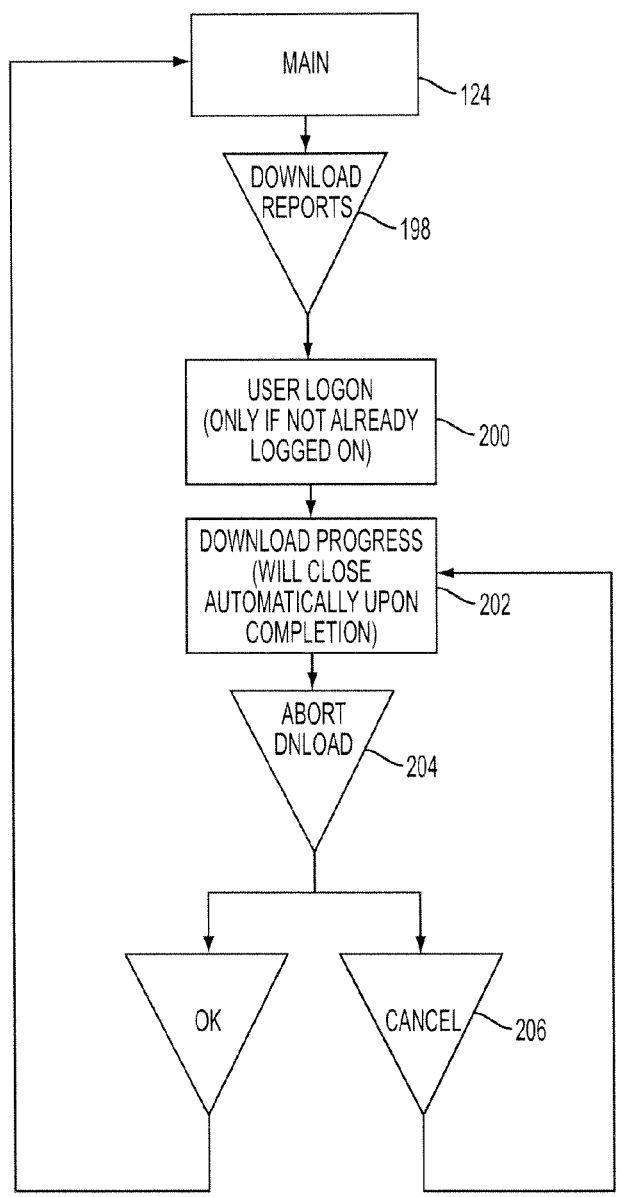
FIG. 16 is a flowchart of the download data function of the client computer software.

FIG. 16. illustrates the download by the first client computer 34 of the results of the data analysis by the server computer 36. The results of the data analysis also may be downloaded by an authorized person using a second client computer 35. An authorized person, such as a healthcare provider or insurance company, selects 'download reports'198 from the 'main' menu 124. The user logs onto the network 200, assuring the server computer 36 that the person is authorized to receive the requested report. The person instructs the server computer 36 as to the patient information that the person desires to receive. The server computer 36 then transmits the requested information to the first or second client computer 34/35, over the network 38 for display to the authorized person. The first or second client computer 34/35, follows the progress of the download 202. The download may be aborted 204 and the abort may be cancelled 206.

Figure 17:
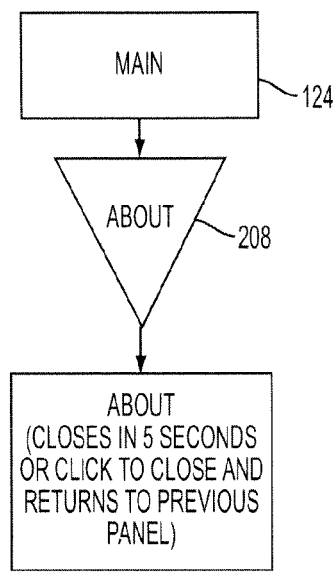
FIG. 17 is a flowchart of the 'about' function of the client computer software.
Figure 18:
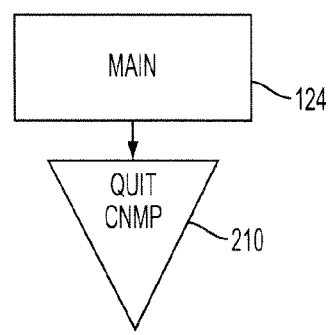
FIG. 18 is a flowchart of the 'quit' function of the client computer software.

From FIGS. 17 and 18, the 'main' menu 124 also allows the user to access an 'about' screen 208 providing information about the software. The main menu also allows the user to 'quit' 210 the program.

The first client computer software 114 provides methods for failure detection and override. If any sensor 4, 6, 8, 10, 12 or cable 48, 58, 70, 72, 74, 76 is detected to be faulty, the first client computer software 114 alerts the user, and allows the user to override the detection, or halt the test to allow for fault correction. The first client computer software 114 also employs data encryption, to ensure the integrity of the CNMP data 30 or ROM data 32.

Figure 19:
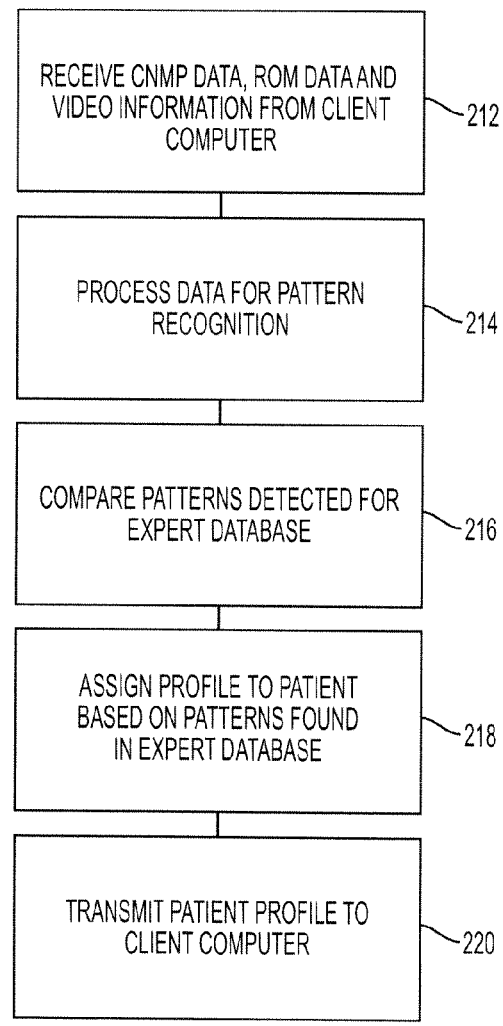
FIG. 19 is a flowchart of the server computer analysis.

FIG. 19 illustrates the operation of the server computer 36 evaluating the CNMP data 30 and ROM data 32. In step 212 of FIG. 18, server computer 36 receives ROM data 32. The ROM data 32 comprises information relating to range of motion of a body part of the patient 46 and the dynamic motion of the patient 46 within that range. The server computer also receives CNMP data 30 comprising pinch data 88, grip data 86, isometric function data 84 and EMG data 82. The server computer microprocessor 118 is programmed to perform pre-determined data evaluation on the data received. As indicated on step 214 of FIG. 19, the data evaluation comprises pattern recognition evaluation using techniques as known in the art, either alone or in combination. The evaluation of the data may reveal patterns in the CNMP data 30 and ROM data 32. As indicated on step 216 of FIG. 18, the server microprocessor 118 consults an expert database 122 of patterns and combinations of patterns resident in server computer memory 120. The expert database 122 associates one or more diagnoses, or patient profiles 40, with each of the patterns or combinations of patterns. From step 218, the expert database 122 informs the server microprocessor 118 of the patient profile 40 identified by the patterns and combination of patterns. From step 220, the server microprocessor 118 supplies a report of the patient profile 40 to the user or other authorized person over the computer network 38.

Evaluation and analysis of the data collected by the first client computer 34 may be performed in whole or in part by a human expert. During collection of data for creation of the expert database, an expert physician will review all results of the analysis and the expert database will be amended to incorporate the results of the physician's review. Once the system has a large track record, only abnormal patterns detected during the analysis will be referred for expert physician review.

The Invention is designed to provide medical professionals and other interested parties with an accurate method of simultaneously observing muscular functionality and additional muscular and nervous system characteristics. This will provide the users a pinpoint procedure to identify and properly diagnose myofascial and other injuries. The Invention achieves its goals through combining surface EMG and pulsed DC electromagnetic range-of-motion technology, along with isometric functional capacity and grip/pinch strength sensors, to obtain a comprehensive set of necessary functional output signals. The Invention uses a custom signal conditioning and conversion circuit board 78 to condition and digitize the signals, which are then fed to a first client computer 34.

The Invention is non-invasive, non-loading and portable. The Invention uses a combination of surface EMG sensors 4, a ROM sensor 6, an isometric function sensor 12, a grip sensor 8 and a pinch sensor 10 in order to determine the functional capability and characteristics of muscle group and surrounding tissues. The EMG sensors 4 obtain readings related to the pathophysiological processes within a muscle, pressure exerted by blood vessels on the muscle and surrounding tissue, as well as observing muscle characteristics such as muscle tone and presence of spasms. The isometric function sensor 12, along with pinch 10 and grip 8 strength sensors allow a higher level of accuracy in identifying certain types of injuries. The isometric function sensor allows the Invention to monitor the patients' potential lifting force. This is a major factor in identifying lower back injuries and in monitoring compliance by the patient 46 with the performance of the test. A person who is feigning injury may be detected through the isometric function data 84 alone or in combination with EMG data 82. The pinch and grip strength sensors 10, 8 accomplish the same task as the isometric function sensor 12, except that the pinch and grip sensors 10, 8 observe the functional characteristics of those body parts which typically correspond to carpel tunnel syndrome and other related injuries. As used in this application, the term "functional capacity data" means data relating to the ability of the patient to exert force using the muscles of the patient and includes isometric function data 84, pinch data 88 and grip data 86.

The Invention uses the combination of different technologies in order to simultaneously monitor muscle groups in order to thoroughly obtain information about muscle functionality, rate of fatigue, muscle response, and other associated muscular characteristics. The simultaneous use of complementary technologies allows the user to accurately monitor the muscular compensation patterns typically seen in injured muscle groups and their surrounding areas. These compensation patterns are usually a key element in identifying the age and type of injury present.

The accuracy of the Invention allows medical professionals to have a much higher degree of certainty when diagnosing injuries. This allows the patient 46 and medical professional to prescribe a more detailed course of action for treatment and rehabilitation, saving time and money. It also allows a higher level of objectivity when diagnosing work-related injuries, saving businesses time and money that would be lost through workers' compensation and ADA-related lawsuits.

The Invention allows for a high level of portability and patient 46 comfort. The pulsed DC electromagnetic ROM sensor 6, transmitter 50 and ROM device signal processing unit 60 provide a more accurate method of obtaining range-of-motion data than previously available, while providing a very compact device which increases the ease of transportation. The use of the electromagnetic device also does not require the use of harnesses or belts to attach the device to the patient. Instead, the device is attached by a single small sensor, in a manner similar to the EMG sensors 4 used by the surface EMG component. This provides the patient 46 with a much more comfortable testing experience, and makes the entire system less cumbersome to use than prior art testing systems.

Use of the Invention is not limited to human injuries and may accurately monitor muscle groups for injury diagnosis in animals, primarily horses.

The Invention may be used to measure actual muscular potential independent of patient effort. The ROM data 32 and surface EMG data 82 in combination allows the Invention to objectively measure the actual range-of-motion or lifting potential of the patient 46, reducing the likelihood of false discrimination cases and workers' compensation claims.

The Invention also may differentiate between related injuries. This includes related injuries such as paraspinal and herniated discs, vasoconstriction, and carpal tunnel syndrome and cubital tunnel syndrome. The use of simultaneous monitoring allows for the observation of compensation patterns and additional inter-muscle relations, which assists in the differentiation process. The Invention may assist in pre-employment screening, in order to provide pre and post-injury comparison. The apparatus also may monitor injury healing during the rehabilitation process. The apparatus may be used in the athletic community, allowing the monitoring of rate of muscle fatigue, and allowing a diagnosis of muscle relationships and the subsequent strengths and weaknesses in an athletes' makeup.

The server computer may be equipped and programmed to create a permanent record of the protocol data collected concerning a patient, such as by creating CDs or DVDs or by utilizing other storage means known in the art.

The invention may be adapted to collect and to analyze electrocardiogram ("EKG") information.

A copy of the source code for the first client computer software 114, written in the LabVIEW language and recorded on a CD ROM, is attached hereto and incorporated by reference herein.

Although this invention has been described and illustrated by reference to specific embodiments, it will be apparent to those skilled in the art that various changes and modifications may be made which clearly fall within the scope of this invention. The present invention is intended to be protected broadly within the spirit and scope of the appended claims.

We claim:

1. An apparatus for generating neuromuscular profile data for a patient, the apparatus comprising:
    an EMG device for generating an EMG signal for a patient;
    a ROM device for generating a ROM signal for a patient, said ROM device utilizing a remote sensing technology;
    a signal processing unit including a ROM signal processing device for converting the ROM signal into ROM data and a signal processing device for converting the EMG signal to EMG data the signal processing unit further including a first data output terminal for outputting the EMG data and a second data output terminal for outputting the ROM data, the first data output terminal being separately provided in the signal processing unit from the second data output terminal;
    a client computer having a computer memory, said client computer being operatively connected to said EMG device and said ROM device via said signal processing unit, said client computer being configured to receive said EMG data and said ROM data and to store said EMG data and said ROM data in said computer memory; and
    a server computer including an expert system configured to evaluate said EMG data and said ROM data and an expert database, the expert system utilizing a pattern comparison method, wherein:
    in the pattern comparison method, the server computer is configured to extract patterns from said EMG data and said ROM data and to compare the extracted patterns with patterns in the expert database, and
    the client computer is configured to receive said ROM data output from the second data output terminal via a channel different from a channel for receiving said EMG data output from the first data output terminal.

2. The apparatus of claim 1, wherein said remote sensing technology comprises a pulsed DC electromagnetic field technology, an AC electromagnetic field technology or an optical technology.

3. The apparatus of claim 1, wherein said remote sensing technology comprises a pulsed DC electromagnetic field technology.

4. The apparatus of claim 3, wherein said ROM device utilizing the pulsed DC electromagnetic field technology comprises a ROM transmitter and a ROM sensor,
    said ROM transmitter adapted to be placed in a predetermined relationship with a body of the patient and further adapted to generate an electromagnetic field,
    said ROM sensor adapted to be attached to said body of the patient,
    said ROM sensor being adapted to generate the ROM signal in response to a location of said ROM sensor within said electromagnetic field.

5. The apparatus of claim 1, further comprising:
    an isometric function measurement device for generating an isometric function signal for the patient, wherein:
    said client computer is operatively connected to said isometric function measurement device via the signal processing device.
    the signal processing device converts the isometric function signal to isometric function data, and
    said client computer is configured to receive said isometric function data output from the first data output terminal and to store said isometric function data in said computer memory.

6. The apparatus of claim 1, further comprising:
    a grip strength measurement device for generating a grip strength signal for the patient, wherein:
    said client computer is operatively connected to said grip strength measurement device via the signal processing device,
    the signal processing device converts the grip strength signal to grip strength data, and
    said client computer is configured to receive said grip data output from the first data output terminal and to store said grip data in said computer memory.

7. The apparatus of claim 1, further comprising:
    a finger pinch measurement device for generating a finger pinch signal for the patient, wherein:
    said client computer is operatively connected to said finger pinch measurement device via the signal processing device,
    the signal processing device converts the finger pinch signal to finger pinch data, and
    said client computer is configured to receive said finger pinch data output from the first data output terminal and to store said finger pinch data in said computer memory.

8. The apparatus of claim 1, further comprising:
    an image input device for generating video information, wherein:
    said client computer is operatively connected to said image input device, and
    said client computer is configured to receive said video information and to store said video information in said computer memory.

9. The apparatus of claim 1, further comprising:
a protocol stored in said computer memory;
said protocol comprising an instruction for a task to be performed by the patient,
said protocol further comprising a specification for protocol data to be collected during performance of said task by the patient, wherein
said client computer is configured to collect and to record said protocol data to said computer memory.

10. The apparatus of claim 9, wherein:
said protocol data relates to one or more of said EMG data, said ROM data, isometric function data, grip data, pinch data or video information.

11. The apparatus of claim 10, wherein said client computer is configured to provide to a user said instruction for said task to be performed by the patient.

12. The apparatus of claim 1, wherein:
the server computer is configured to receive said EMG and ROM data via a computer network,
the server computer is configured to compare said EMG data and ROM data with the expert database for generating a patient profile, and
the server is further configured to send the patient profile to the client computer.

13. An apparatus for generating neuromuscular profile data for a patient, the apparatus comprising:
a signal conditioning and conversion circuit board;
an EMG sensor configured to be attached to the patient at a predetermined EMG sensor location,
said EMG sensor being configured to generate an EMG signal,
said EMG sensor being electrically connected to said signal conditioning and conversion circuit board,
said signal conditioning and conversion circuit board being configured to receive said EMG signal and to convert said EMG signal into EMG data, and
said conditioning and conversion circuit board including a first output terminal for outputting the EMG data;
a ROM transmitter configured to be placed in a predetermined transmitter location with respect to the patient and to generate an electromagnetic field;
a ROM sensor configured to be attached to a body of the patient at a predetermined ROM sensor location and to interact with said electromagnetic field to generate a ROM signal;
a ROM signal processor electrically connected to said ROM sensor,
said ROM signal processor being configured to receive said ROM signal and to convert said ROM signal to ROM data, and
said ROM signal processor including a second output terminal for outputting the ROM data, the second output terminal being provided separately from the first terminal;
a client computer having a computer memory,
said client computer being electrically connected to said signal conditioning and conversion circuit board and to said ROM signal processor, and
said computer being configured to receive said EMG data and said ROM data and to store said EMG data and said ROM data in said computer memory; and
a server computer including an expert system configured to evaluate said EMG data and said ROM data and an expert database, the expert system utilizing a pattern comparison method, wherein:
in the pattern comparison method, the server computer is configured to extract patterns from said EMG data and said ROM data and to compare the extracted patterns with patterns in the expert database, and
the client computer is configured to receive said ROM data output from the second data output terminal via a channel different from a channel for receiving said EMG data output from the first data output terminal.

14. The apparatus of claim 13, wherein:
the server computer is configured to receive said EMG and ROM data via a computer network,
the server computer is configured to compare said EMG data and ROM data with the expert database for generating a patient profile, and
the server is further configured to send the patient profile to the client computer.

15. The apparatus of claim 13, further comprising:
an isometric function sensor configured to generate an isometric function signal in response to a force applied by the patient,
said isometric function sensor being electrically connected to said signal conditioning and conversion circuit board,
said signal conditioning and conversion circuit board being configured to convert said isometric function signal into isometric function data, and
said client computer being configured to receive said isometric function data output from the first data output terminal and to store said isometric function data in said computer memory.

16. The apparatus of claim 15, further comprising:
a grip strength sensor configured to generate a grip signal in response to a grip of the patient,
said grip strength sensor being electrically connected to said signal conditioning and conversion circuit board,
said signal conditioning and conversion circuit board being configured to convert said grip strength signal into grip data, and
said client computer being configured to receive said grip data output from the first data output terminal and to store said grip data in said computer memory.

17. The apparatus of claim 16, further comprising:
a finger pinch strength sensor configured to generate a pinch strength signal in response to a finger pinch of the patient,
said pinch strength sensor being electrically connected to said signal conditioning and conversion circuit board,
said circuit board being configured to convert said finger pinch strength signal into pinch data, and
said client computer being adapted to receive said pinch data output from the first data output terminal and to store said pinch data in said computer memory.

18. The apparatus of claim 17, further comprising:
a video camera configured to generate video information of the patient,
said video camera being electrically connected to said client computer,
said client computer being configured to receive said video information from said signal conditioning and conversion circuit board and to store said video information in said computer memory.

19. The apparatus of claim 13, further comprising:
a protocol, said protocol being resident in said computer memory of said client computer;
said protocol comprising an instruction for a task to be performed by the patient, said protocol further comprising a specification for protocol data to be collected during performance of said task by the patient, said client computer being configured to administer said protocol and to collect said protocol data.

20. The apparatus of claim 19, wherein said protocol data comprises one or more of said EMG data, said ROM data, isometric function data, grip data, pinch data or video information.

21. The apparatus of claim 20, wherein said client computer is configured to provide to a user said instruction for said task to be performed by the patient.

22. A method for collecting neuromuscular data for a patient, the method comprising the steps of:
- generating an EMG signal for the patient;
- generating a ROM signal for the patient, said ROM data being generated using a remote sensing technology;
- converting the EMG signal into EMG data and outputting the EMG data from a first data output terminal;
- converting the ROM signal into ROM data and outputting the ROM data from a second data output terminal, the second output terminal being provided separately from the first terminal;
- receiving the ROM data output from the second data output terminal via a channel different from a channel for receiving the EMG data output from the first data output terminal;
- storing said EMG data and said ROM data in a computer memory;
- comparing said EMG data and said ROM data by utilizing an expert system including an expert database, said expert database associating a profile with said combination of said EMG data and said ROM data, the expert system utilizing a pattern comparison method;
- evaluating said EMG data and ROM data by consulting said expert database for generating a profile for said patient; and
- communicating to a user said profile for said patient, wherein
- in the step of comparing, patterns are extracted from said EMG data and said ROM data and the extracted patterns are compared with patterns in the expert database.

23. The method of claim 22, wherein said remote sensing technology is selected from the group consisting of a pulsed DC electromagnetic field technology, an AC electromagnetic field technology and an optical technology.

24. The method of claim 23, wherein said remote sensing technology comprises a pulsed DC electromagnetic field technology.

25. The method of claim 24, further comprising the steps of:
- generating functional capacity data for the patient; and
- recording said functional capacity data in said computer memory.

26. The method of claim 25, wherein said functional capacity data comprises pinch data, grip data and isometric function data.

* * * * *